United States Patent
Moll

(10) Patent No.: US 7,271,001 B2
(45) Date of Patent: Sep. 18, 2007

(54) METHOD FOR MITOCHONDRIAL TARGETING OF P53

(75) Inventor: Ute Moll, Setauket, NY (US)

(73) Assignee: The Research Foundation of State University of New York, Albany, NY (US)

( * ) Notice: Subject to any disclaimer, the term of this patent is extended or adjusted under 35 U.S.C. 154(b) by 0 days.

(21) Appl. No.: 11/009,357

(22) Filed: Dec. 10, 2004

(65) Prior Publication Data

US 2006/0127376 A1      Jun. 15, 2006

(51) Int. Cl.
  *C12N 15/09*   (2006.01)
  *C12N 15/63*   (2006.01)
  *C12N 15/85*   (2006.01)
  *C12N 15/86*   (2006.01)

(52) U.S. Cl. .................... 435/455; 435/320.1; 435/325

(58) Field of Classification Search ................ 514/44; 435/455, 320.1, 325
  See application file for complete search history.

(56) References Cited

OTHER PUBLICATIONS

Mihara et al,(Molecular Cell, 11: 577-590, Mar. 2003.*
Marchenko et al, JBC, 276(21): 16202-16212, 2000.*
Foster et al., 1999. "Pharmacological rescue of mutant p53 conformation and function," Science 286:2507-2510.
Bykov et al., 2002. "Restoration of the tumor suppressor function to mutant p53 by a low-molecular-weight compound," Nat Med 8:282-288.
Moll, 2000. New p53-based strategies for cancer therapy. Eaton Publishing, Natick, MA. 439-455 (BOOK).
Zeimet et al., 2003. "Why did p53 gene therapy fail in ovarian cancer?," Lancet Oncol. 4:415-422.
Nemunaitis et al., 2000. "Adenovirus-mediated p53 gene transfer in sequence with cisplatin to tumors of patients with non-small-cell lung cancer," J Clin. Oncol. 18:609-622.
Kuball et al., 2002 "Successful adenovirus-mediated wild-type p53 gene transfer in patients with bladder cancer by intravesical vector instillation," J Clin Oncol. 20:957-965.
Vecil and Lang, 2003."Clinical trials of adenoviruses in brain tumors: a review of Ad-p53 and oncolytic adenoviruses," J Neuro. Oncol. 65:237-246.
Herman and Baylin. 2003 "Gene silencing in cancer in association with promoter hypermethylati,". N Eng. J Med 349:2042-2054.
Concin et al., I. 2004. "Transdominant DeltaTAp73 isoforms are frequently up-regulated in ovarian cancer. Evidence for their role as epigenetic p53 inhibitors in vivo," Cancer Res 64:2449-2460.
Moll et al., 2001 "p53, p63 and p73—solos, alliances and feuds among family members," Biochim Biophys Acta 1552:47-59.
Schuler and Green. 2001 "Mechanisms of p53-dependent apoptosis," Biochem Soc Trans 29:684-688.
Moll UM, Slade N. 2004 "p63 and p73: roles in development and tumor formation," Mol Cancer Res 2: 371-386.

Luo et al., 2001, Knock-in mice with a chimeric human/murine p53 gene develop normally and show wild-type p53 responses to DNA damaging agents: a new biomedical research tool.
Jacobson et al., "Programmed cell death and Bcl-2 protection in the absence of a nucleus," Embo J 13:1899-1910 (1994).
Martin et al., 1996 "Phosphatidylserine externalization during CD95-induced apoptosis of cells and cytoplasts requires ICE/CED-3 protease activity.," J Biol Chem 271 :28753-28756.
Schulze-Osthoff et al., 1994 "Cell nucleus and DNA fragmentation are not required for apoptosis," J Cell Biol. 127: 15-20.
Marchenko et al., Moll. 2000 "Death signal-induced localization of p53 protein to mitochondria. A potential role in apoptotic signaling," J Biol Chem. 275:16202-16212.
Sansome et al., Moll. 2001 "Hypoxia death stimulus induces translocation of p53 protein to mitochondria. Detection by immunofluorescence on whole cells," FEBS Lett. 488: 110-115.
Mihara et al., Moll. 2003 "p53 has a direct apoptogenic role at the mitochondria," Molecular Cell, 11: 577-790.
Mihara et al., 2003 "Detection of mitochondrial localization of p53," Methods Mol Biol 234:203.
Petros et al., 2004. FEBS Letters 28073:1-4.
Schmitt et al., 1999, "INK4a/ARF mutations accelerate lymphomagenesis and promote chemoresistance by disabling p53.," Genes Dev 13:2670-2677.
Schmitt et al., 2000 "Genetic analysis of chemoresistance in primary murine lymphomas," Nat Med 6:1029-1035.
Eischen et al., 2001 "Bax loss impairs Myc-induced apoptosis and circumvents the selection of p53 mutations during Myc-mediated lymphomagenesis.," Mol Cell Biol 21:7653-7662.
Eischen et al., 2001 "Apoptosis triggered by Myc-induced suppression of Bcl-X (L) or Bcl-2 is bypassed during lymphomagenesis," Mol Cell Biol 21:5063-5070.
Eischen et al., 1999 "Disruption of the ARF-Mdm2-p53 tumor suppressor pathway in Myc-induced lymphomagenesis," Genes Dev 13:2658-2669.
Jacobs et al., 1999 "Bmi-1 collaborates with c-Myc in tumorigenesis by inhibiting c-Myc-induced apoptosis via INK4a/ARF" Genes Dev. 13:2678-2690.
Lindenboim et al., 2001 "Bcl-x(S) can form homodimers and heterodimers and its apoptotic activity requires localization of Bcl-x(S) to the mitochondria and its BH3 and loop domains,", Cell Death Differ 8:933-942.
Boise et al., L.H., 1993 "bcl-x, a bcl-2-related gene that functions as a dominant," Cell 74:597-608.

(Continued)

*Primary Examiner*—Deborah Crouch
*Assistant Examiner*—Magdalene Sgagias
(74) *Attorney, Agent, or Firm*—Medlen & Carroll, LLP

(57) ABSTRACT

The present invention relates to methods and compositions for modulating apoptotic pathways. In particular, the present invention relates to methods and compositions for inducing apoptosis in cancer cells. The present invention further relates to methods and compositions for identifying drugs that modulate apoptotic pathways.

11 Claims, 21 Drawing Sheets

OTHER PUBLICATIONS

Moll, et al., 2001, Nuclear and mitochondrial apoptotic pathways of p53, "FEBS Lett", Mar. 30;493(2-3): 65-9 Review.

Erster, et al. 2004, In vivomitochondrial p53 translocation triggers a rapid first wave of celldeath in repsonse to DNA damage that can precede p53 target gene activation. Mol Cell Biol.Aug. 24 (15): 6728-41.

Erster, et al., 2004, Stress-induced p53 runs a direct mitochondrial death program: its role in physiologic and pathophysiologic stress responses in vivo. "Cell Cycle", December;3(12):1492-5.

Moll, et al., 2001, Nuclear and mitochondrial apoptotic pathways of p53. FEBS Lett, Mar. 30; 493(2-3): 65-9 Review.

\* cited by examiner

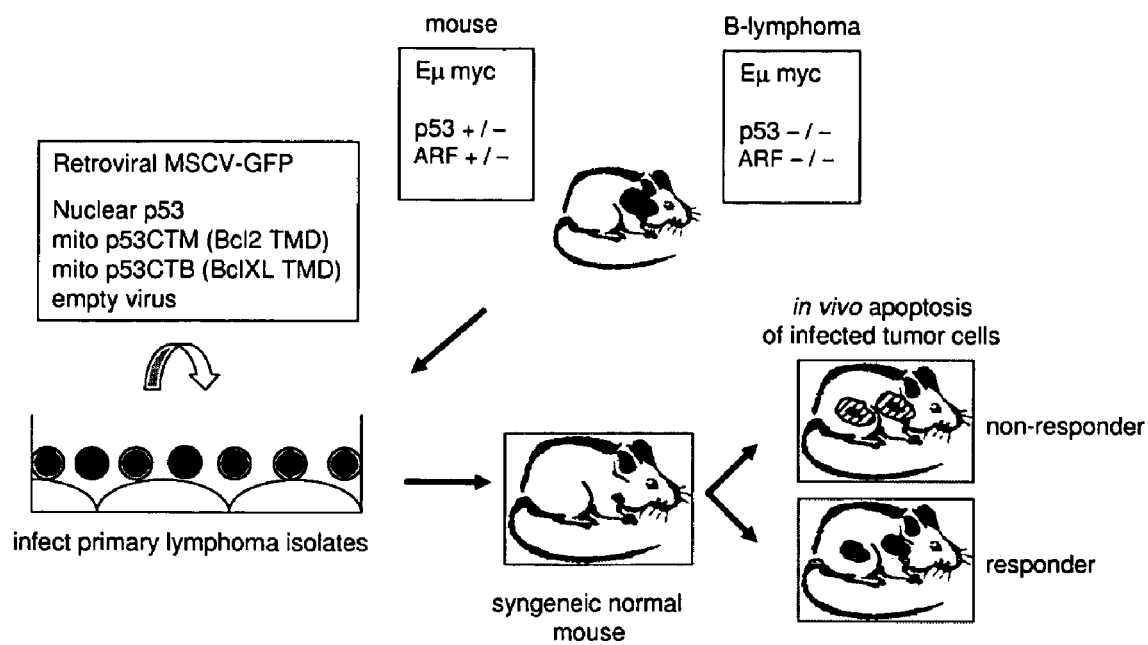
Figure 1 Treatment response in Eμ myc lymphoma

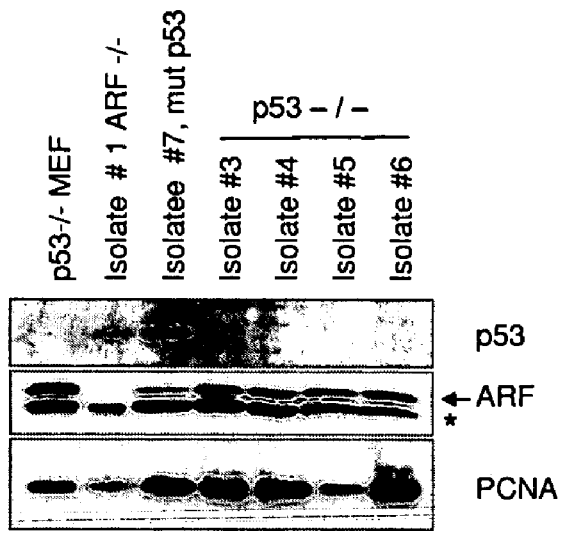
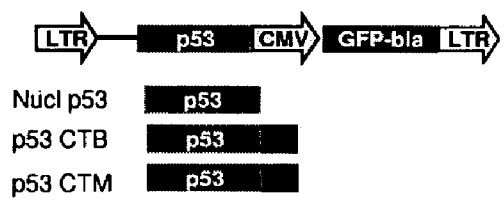
Figure 2a

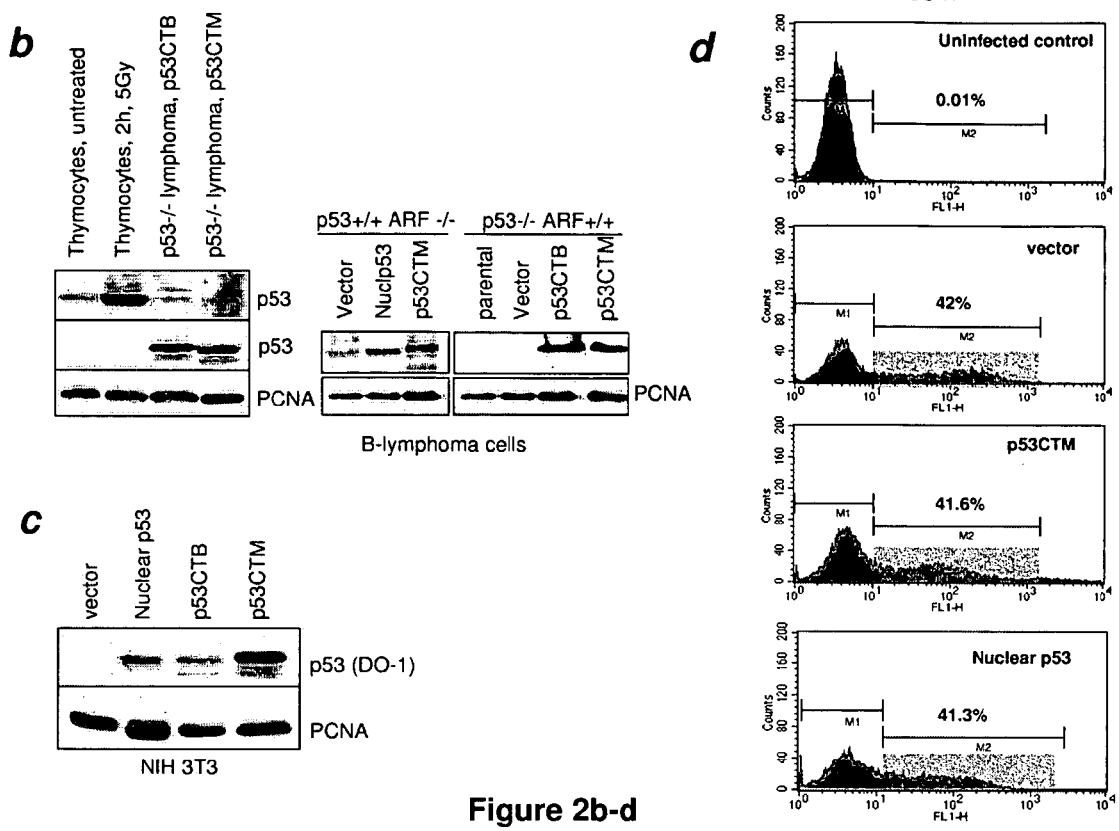
Figure 2b-d

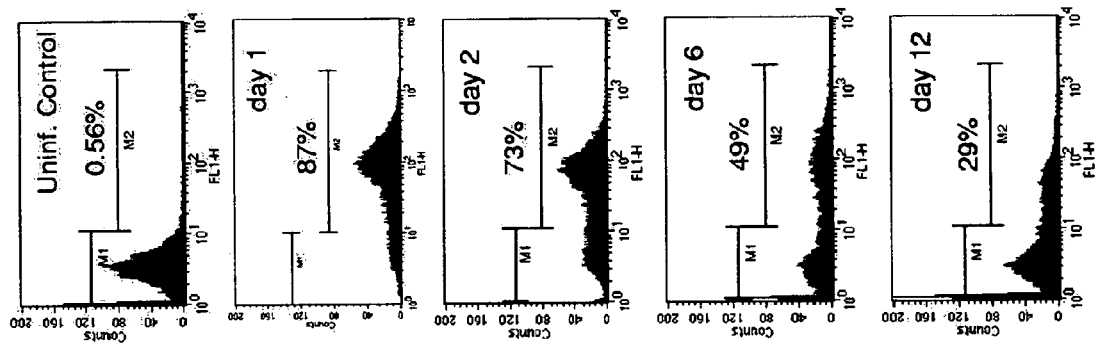
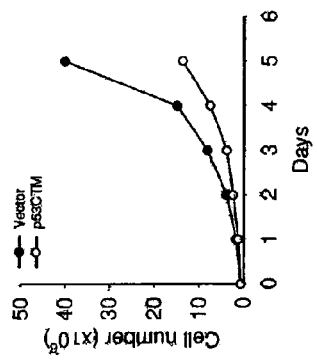
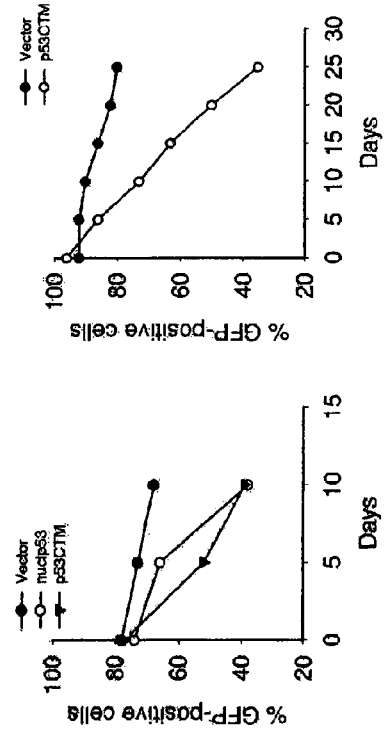
Figure 4a-b

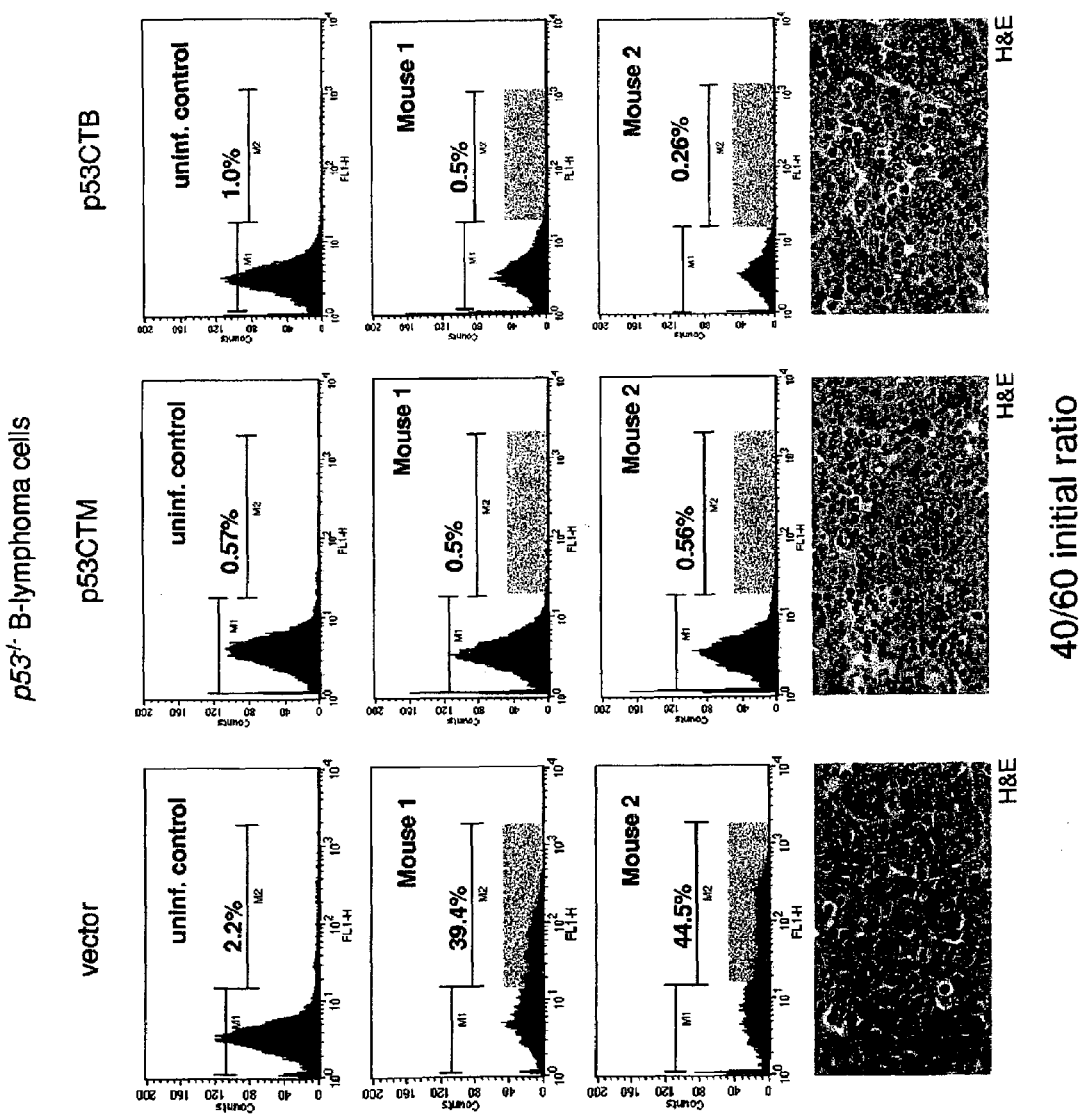

Figure 9
p53CTB, nucleic acid sequence (SEQ ID NO: 1)

```
    1                      cc tccatccgcc ccgtctctcc ccttgaacct cctcgttcga cccgcctcg
   61 atcctccctt tatccagccc tcactccttc tctaggcgcc ggaattcctg cagcccggg
  121 ggtccatgga ggagccgcag tcagatccta gcgtcgagcc ccctctgagt caggaaacat
  181 tttcagacct atggaaacta cttcctgaaa acaacgttct gtcccccttg ccgtcccaag
  241 caatgatga tttgatgctg tcccccgacg atattgaaca atggttcact gaagacccag
  301 gtccagatga agctcccaga atgccagagg ctgctcccg cgtggcccct gcaccagcag
  361 ctcctacacc ggcggcccct gcaccagccc gcacctgcc cctgtcatct tctgtccctt
  421 cccagaaaac ctaccagggc agctacggtt tccgtctggg cttcttgcat tctggacag
  481 ccaagtctgt gacttgcacg tactccctg ccctcaacaa gatgttttgc caactggcca
  541 agacctgccc tgtgcagctg tgggttgatt ccacacccc gcccggcacc cgcgtccgcg
  601 ccatggccat ctacaagcag tcacagcaca tgacggaggt tgtgaggcgc tgccccacc
  661 atgagcgctg ctcagatagc gatggtctgg ccctcctca gaaacactt tgtgagggag cgagtggaag
  721 gaaatttgcg tgtggagtat ttggatgaca gaaacacctt tcgacatagt gtggtggtgc
  781 cctatgagcc gcctgaggtt ggctctgact gtaccaccat cctactacaac tacatgtgta
  841 acagttcctg catggcggc atgaaccgga ggcccatcct caccatcatc acactgtgaag
  901 actccagtgg taatctactg ggacgaaca gctttgagt gcgtgtttgt gcctgtcctg
  961 ggagagaccg gcgcacagag gaagagaatc tccgcaagaa aggggagcct caccacgagc
 1021 tgccccccagg gagcactaag cgagcactgc ccaacaacac cagtcctct cccagccaa
 1081 agaagaaacc actgatgga gaatatttca ccctttcagat cgtgggcgt gagcgcttcg
 1141 agatgttccg agagtgaat gaggccttgg aactcaagga tgcccaggct gggaaggagc
 1201 cagggggag cagggctcac tccagccacc tgaagtccaa aaagggtcag tctacctccc
 1261 gccataaaaa acttcatgttc aagacagaag ggcctgactc agatctaagc cgaaagggcc
 1321 aggaacgctt caaccgctgg ttcctgacgg gcatgactgt ggccggcgtg gttctgctgg
 1381 gctccactctt cagtcggccg ctttacggtt ctggcctt tgctggagac
``` atg is translational start site
tga is translational stop site

Figure 10
p53CTB, amino acid sequence (SEQ ID NO: 2)

```
118 ATGGAGGAGCCGCAGTCAGATCCTAGCGTCGAGCCCCCTCTGAGT
      M  E  E  P  Q  S  D  P  S  V  E  P  P  L  S
163 CAGGAAACATTTTCAGACCTATGGAAACTACTTCCTGAAAACAAC
      Q  E  T  F  S  D  L  W  K  L  L  P  E  N  N
208 GTTCTGTCCCCCTTGCCGTCCCAAGCAATGATGATTTGATGCTG
      V  L  S  P  L  P  S  Q  A  M  D  D  L  M  L
253 TCCCCGGACGATATTGAACAATGTTCACTGAAGACCCAGGTCCA
      S  P  D  D  I  E  Q  W  F  T  E  D  P  G  P
298 GATGAAGCTCCCAGAATGCCAGAGGCTGCTCCCCGGGTGGCCCCT
      D  E  A  P  R  M  P  E  A  A  P  R  V  A  P
343 GCACCAGCAGCTCCTACACCGGCCGCCCCTGCACCAGCCGCCTCC
      A  P  A  A  P  T  P  A  A  P  A  P  A  P  S
388 TGGCCCCTGTCATCTTCTGTCCCTTCCCAGAAAACTACCAGGGC
      W  P  L  S  S  S  V  P  S  Q  K  T  Y  Q  G
433 AGCTACGGTTTCCGTCTGGGCTTCTTGCATTCTGGACAGCCAAG
      S  Y  G  F  R  L  G  F  L  H  S  G  T  A  K
478 TCTGTGACTTGCACGTACTCCCCTGCCCTCAACAAGATGTTTTGC
      S  V  T  C  T  Y  S  P  A  L  N  K  M  F  C
523 CAACTGGCCAAGACCTGCCCGTGCAGCTGTGGGTTGATTCCACA
      Q  L  A  K  T  C  P  V  Q  L  W  V  D  S  T
568 CCCCCGCCCGGCACCCGGGTCCGGCGCCATGGCCATTACAAGCAG
      P  P  P  G  T  R  V  R  A  M  A  I  Y  K  Q
613 TCACACACATGACGGAGGTTGTGAGGCGCTGCCCCCACCATGAG
      S  Q  H  M  T  E  V  V  R  R  C  P  H  H  E
658 CGCTGCTCAGATAGCGATGGTCTGGCCCCTCCTCAGCATCTTATC
      R  C  S  D  S  D  G  L  A  P  P  Q  H  L  I
703 CGAGTGGAAGGAAATTTGCGTGTGGAGTATTTGGATGACAGAAAC
      R  V  E  G  N  L  R  V  E  Y  L  D  D  R  N
```

Figure 10 continued

```
 748  ACTTTTCGACATAGTGTGTGGTGCCCTATGAGCCGCCTGAGGTT
       T  F  R  H  S  V  V  P  Y  E  P  P  E  V
 793  GGCTCTGACTGTACCACCATCCACTACAACTACATGTGTAACAGT
       G  S  D  C  T  T  I  H  Y  N  Y  M  C  N  S
 838  TCCTGCATGGGCGGCATGAACCGGAGGCCCATCCTCCACCATCATC
       S  C  M  G  G  M  N  R  R  P  I  L  T  I
 883  ACACTGGAAGACTCCAGTGGTAATCTACTGGGACGGAACAGCTTT
       T  L  E  D  S  S  G  N  L  L  G  R  N  S
 928  GAGGTGCGTGTTTGTCCTGTCCTGCAAGAAAGGGAGCCTCACCAGCTGCCC
       E  V  R  V  C  A  C  P  G  R  D  R  R  T  E
 973  GAAGAGAATCTCCGCAAGAAAGGGAGCCTCACCACCAGCTGCCC
       E  E  N  L  R  K  K  G  E  P  H  H  H  L  P
1018  CCAGGGAGCACTAAGCGACACTGCCCAACACCAGCTCTCT
       P  G  S  T  K  R  A  L  P  N  N  T  S
1063  CCCCAGCCAAAGAGAAACCACTGGATGGAGAATATTTCACCTTT
       P  Q  P  K  K  K  P  L  D  G  E  Y  F  T  L
1108  CAGATCCGTGGGCGTGAGCGCTTCGAGATGTTCCGAGAGCTGAAT
       Q  I  R  G  R  E  R  F  E  M  F  R  E  L  N
1153  GAGGCCTTGGAACTCAAGGATGCCCAGGCTGGAAGGAGCCAGGG
       E  A  L  E  L  K  D  A  Q  A  G  K  E  P  G
1198  GGGAGCAGGGCTCACTCAGCACTGAAGTCCAAAAAGGGTCAG
       G  S  R  A  H  S  S  H  L  K  S  K  G  Q
1243  TCTACCTCCCGCCATAAAAACTCATGTTCAAGACAGAAGGGCCT
       S  T  S  R  H  H  K  K  L  M  F  K  T  E  P
1288  GACTCAGATCTAAGCGGAAGGGCCAGGAACGCTTCAACCGCTGG
       D  S  D  L  S  R  K  G  Q  E  R  F  N  R  W
1333  TTCCTGACGGGCATGACTGTGGCCGGCGTGGTTCTGCTGGGCTCA
       F  L  T  G  M  T  V  A  G  V  V  L  L  G  S
1378  CTCTTCAGTCGGAAATGA  1395
       L  F  S  R  K  *
```

FIGURE 11

Table I. In vivo killing of lymphoma cells expressing mitochondrially targeted p53

| Retroviruses injection | injected B-lymphoma cells | injected/ number of independent experiments | mice with tumors | tumor weight (g) | Tumor cells GFP-positive# at 28-30 days post- |
|---|---|---|---|---|---|
| *p53-null B-cells* | | | | | |
| No pre-selection, no sorting | | # 2, 3, 4 and 5 9 indep. expts. | | | |
| Vector - GFP | 40/60 | | 18 | 1.0 +/-0.2 | 30.8 +/- 18% |
| NucIp53 - GFP | 40/60 | | 12 | 0.7 +/-0.3 | 0%* |
| p53CTM - GFP | 40/60 | | 14 | 1.0 +/-0.4 | 0.4 +/- 1.0%** |
| p53CTB - GFP | 40/60 | | 4 | 0.4 +/-0.1 | 0%* |
| Blasticidine pre-selection | | # 2, 4 and 5 3 indep. expts. | | | |
| Vector - GFP | 75/25 | | 3 | 0.7 +/-0.2 | 44.3 +/- 3% |
| NucIp53 - GFP | 75/25 | | 1 | 0.5 | 12%@ |
| p53CTM - GFP | 75/25 | | 11 | 0.6 +/-0.4 | 1.1 +/- 0.1% * |

FIGURE 12

Table II. In vivo killing of lymphoma cells expressing mitochondrially targeted p53

*ARF-null B-cells*
No pre-selection, no sorting

| | | # 1 and 2<br>2 indep. expts. | | |
|---|---|---|---|---|
| Vector - GFP | 40/60 | 14 | 0.9 +/-0.4 | 18 +/- 13% |
| Nuclp53 - GFP | 40/60 | 13 | 0.33 +/- 0.2 | 0.6% +/- 0.6 |
| p53CTM - GFP | 40/60 | 12 | 0.23 +/-0.1 | 0.2 +/- 0.4%** |
| p53CTB - GFP | 40/60 | 11 | 0.37 +/-0.2 | 0.4 +/- 0.7%** |

@ Western analysis showed no p53 expression by this tumor.

Figure 13

Human p53 (SEQ ID NO:6)

```
1   MEEPQSDPSV EPPLSQETFS DLWKLLPENN VLSPLPSQAM DDLMLSPDDI EQWFTEDPGP
61  DEAPRMPEAA PRVAPAPAAP TPAAPAPAPS WPLSSSVPSQ KTYQGSYGFR LGFLHSGTAK
121 SVTCTYSPAL NKMFCQLAKT CPVQLWVDST PPPGTRVRAM AIYKQSQHMT EVVRRCPHHE
181 RCSDSDGLAP PQHLIRVEGN LRVEYLDDRN TFRHSVVVPY EPPEVGSDCT TIHYNYMCNS
241 SCMGGMNRRP ILTIITLEDS SGNLLGRNSF EVRVCACPGR DRRTEEENLR KKGEPHHELP
301 PGSTKRALPN NTSSSPQPKK KPLDGEYFTL QIRGRERFEM FRELNEALEL KDAQAGKEPG
361 GSRAHSSHLK SKKGQSTSRH KKLMFKTEGP DSD
```

Human BclXl (SEQ ID NO:7)

```
1   MSQSNRELVV DFLSYKLSQK GYSWSQFSDV EENRTEAPEG TESEMETPSA INGNPSWHLA
61  DSPAVNGATG HSSSLDAREV IPMAAVKQAL REAGDEFELR YRRAFSDLTS QLHITPGTAY
121 QSFEQVVNEL FRDGVNWGRI VAFFSFGGAL CVESVDKEMQ VLVSRIAAWM ATYLNDHLEP
181 WIQENGGWDT FVELYGNNAA AESRKGQERF NRWFLTGMTV AGVVLLGSLF SRK
```

Human Bcl2 (SEQ ID NO:8)

```
1   MAHAGRTGYD NREIVMKYIH YKLSQRGYEW DAGDVGAAPP GAAPAPGIFS SQPGHTPHTA
61  ASRDPVARTS PLQTPAAPGA AAGPALSPVP PVVHLTLRQA GDDFSRRYRR DFAEMSRQLH
121 LTPFTARGRF ATVVEELFRD GVNWGRIVAF FEFGGVMCVE SVNREMSPLV DNIALWMTEY
181 LNRHLHTWIQ DNGGWDAFVE LYGPSMRPLF DFSWLSLKTL LSLALVGACI TLGAYLGHK
```

Figure 14 p53 (SEQ ID NO:3)

```
   1 cgtgctttcc acgacggtga cacgcttccc tggattggcc agactgcctt ccggtcact
  61 gccatggagg agccgcagtc agatcctagc gtcgagcccc ctctgagtca ggaaacattt
 121 tcagacctat ggaaactact tcctgaaaac aacgttctgt cccccttgcc gtcccaagca
 181 atggatgatt tgatgctgtc ccggacgat attgaacaat ggttcactga agacccaggt
 241 ccagatgaag ctcccagaat gccagaggct gctccccgcg tggcccctgc accagcagct
 301 cctacaccgg cggccctgc accagcccc tctgcgtttc tgtcatcttc tgtcccttcc
 361 cagaaaacct accaggcag ctacgtttc cgtctgggct cttgcattc tgggacagcc
 421 aagtctgtga cttgcacgta ctcccctgcc ctcaacaaga tgttttgcca actggccaag
 481 acctgccctg tgcagctgtg ggttgattcc acaccccgc cggcacccg cgtccgcgcc
 541 atggccatct acaagcagtc acagcacatg tgtctggcc tcctccagc cctcctcagc
 601 gagcgctgct cagatagcga tggtctgcga cctgactg ggatgacaga acactttcac gacatagtgt ggtggtgccc
 661 aatttgcgtg tggagtattt ggatgacaga ctctgactgt aacactttc gacatagtgt ggtggtgccc
 721 tatgagccgc ctgaggttgg ctctgactgt accaccatcc actacaacta catgtgtaac
 781 agttcctgca tgggcggcat gaaccgagg cccatcctca tttgagtgc atgtttgtgc ctgtcctggg
 841 tccagtggta atctactggg acggaacagc tttgaggtgc atgtttgtgc ctgtcctggg
 901 agagaccggc gcacagagga agagaatctc cgcaagaaag gggagcctca ccacgagctg
 961 cccccaggga gcactaagcg agcactgtcc aacaacacca gctcctctcc ccagccaaag
1021 aagaaaccac tggatggaga atatttcacc cttcagatcc gtgggcgtga gcgcttcgag
1081 atgttccgag agctgaatga ggccttggaa ctcaaggatg ccaggctgg gaaggagcca
1141 gggggagca ggctcactc cagcacctg aagtccaaaa agggtcagtc tacctccgc
1201 cataaaaaac tcatgttcaa gacagaaggg cctgactcag actgacattc tccacttctt
1261 gttcccact gacagcctc caccccatc gtcagaagca ctgcattt gggtttttggg
1321 tctttgaacc cttgcttgca ataggtgtgc gtcactggtg tgcagctt ccatttgctt
1381 tgtcccgggg ctccactgaa caagttggcc tgcactggtg tttgttgtg gggaggaga
1441 tgggagtag gacataccag cttagatttt aaggttttta cgtgaggga tgtttgggag
1501 atgtaagaaa tgttcttgca gttaagggtt agttacaat cagccacatt ctctaacttc
1561 gccacttca ccgtactaac caggaagct gtcctcact gtcaatttt gttgaatttt ctctaacttc
1621 aaggcccata tctgtgaaat gctggcattt gcacctacct cacagagtgc attgtgaggg
1681 ttaatgaaat aatgtacatc tggccttgaa accaccttt attacatggg gtctagaact
1741 tgaccccctt gagggtgctt gttccctctc cctgttggtc ggtgggttgg tagtttctac
```

Figure 14 continued

```
1801 agtgggcag ctggttaggt agagggagtt gtcaagtctc tgctggccca gccaaaccct
1861 gtctgacaac ctcttggtga acctagtac ctaaaggaa ctataccc atccacacc
1921 ctggaggatt tcatctcttg tatatgatga tctgatcca ccaagacttg tttatgctc
1981 aggtcaatt tcttttttct ttttttctt tttttcttt tcctttgaga ctgggtctcg
2041 ctttgttgcc caggctggag tggagtggcg tgatcttggc ttactgcagc cttgcctcc
2101 ccggctgag cagtcctgcc tcagcctccg gagtagctgg gaccacaggt tcatgccacc
2161 atgccagcc aactttgca tgttttgtag agatggggtc tcacagtgtt gcccaggctg
2221 gtctcaaact cctggctca ggcgatccac ctgtccagc ctcccagagt gctgggatta
2281 caattgtgag ccaccacgtc cagctgaag ggtcaacatc tttacattc tgcaagcaca
2341 tctgcatttt caccccacc ttcccctcct tctccctttt tatatcccat ttttatatcg
2401 atctcttatt ttacaataaa actttgctgc caaaaaaaaa aaaaaaaaa a
```

Bcl2 (SEQ ID NO:4)

```
  1 atggcgcacg ctgggagaac agggtacgat aaccgggaga tagtgatgaa gtacatccat
 61 tataagctgt cgcagagggt ctacgagtgg gatgcgggag atgtgggcgc cgcgccccg
121 gggccgccc ccgcgccgg ccgcgccgga catctctcc tcgcagcccg ggcacacgcc ccatacagcc
181 gcatcccggg acccggtcgc caggacctcg ccgctgcaga cccggctgc acctgaccct cccggcgcc
241 gccgcgggc ctgcgctcag ccggtgcca cctggtcc gacttcgccg agatgtccag ccagctgcac
301 ggcgacgact tctccccgcg ctaccgcgcg gggacgcgtc gccacggtgg tgagagct cttcagggac
361 ctgacgcct tcaccgcgcg gggagcgct gtgccttc tttgagttcg gtgggtcat gtgtgtggag
421 gggtgaact ggggaggat tgtgccctgg gcccctggtg gacaacatcg ccgtgtggat gactgagtac
481 agcgtcaacc ctgaaccgg acctgcacac ctggatccag gataacggag gctgggatgc ctttgtggaa
541 ctgaaccggc actgatgcg gcctctgttt gcctctgct gatttctcct ggctgtctct gaagactctg
601 ctgtacggcc ccagcatgcg ccagcatgcc gcctctgttt gcctctgct gatttctcct ggctgtctct gaagactctg
601 ctgtacggcc ccagcatgcg ccagcatgcg gcctctgtt acctggtg agctgcatc accctggtg cctatctggg ccacaagtga
661 ctcagtttgg cctggtgggg agctgcatc acctggtg cctatctggg ccacaagtga
```

BclXl (SEQ ID NO:5)

```
  1 atgtcccaga gcaaccggga gctgtggtt gactttctct cctacaagct tccagaaa
 61 ggatacagct ggagtcagtt tagtgatgtg gaagagaaca ggactgaggc ccagaaggg
121 actgaatcgg agatggagac cccagtgcc atcaatggca accatcctg gcacctggca
181 gacagccccg cggtgaatgg agccactggc cacagcagca gttggatgc ccgggaggtg
241 atccccatgg cagcagctaa gcaagcgctg agggaggcag gcgacgagtt tgaactgcgg
301 taccgcgggg cattcagtga cctgacatcc cagctccaca tcacccagg cagctccaca tcagctgcag
```

Figure 14 continued

```
361 cagagctttg aacaggtagt gaatgaactc ttccgggatg gggtaaactg gggtcgcatt
421 gtggcctttt tctccttcgg cgggcactg tgcgtggaaa gcgtagacaa ggagatgcag
481 gtattggtga gtcggatcgc agcttggatg gccacttacc tgaatgacca cctagagcct
541 tggatccagg agaacgcgg ctgggatact tttgtggaac tctatgggaa caatgcagca
601 gccgagagcc gaaagggcca ggaacgcttc aaccgctggt tcctgacggg catgactgtg
661 gccggcgtgg ttctgctggg ctcactcttc agtcggaaat ga
```

FIGURE 15

Table III. Lack of in vivo killing of lymphoma cells expressing mitochondrially targeted dominant negative mutant p53

| Retroviruses | Ratio of injected B-lymphoma cells | Number of mice with tumors | Average tumor weight (g) | Percent Tumor cells GFP-positive at 28-30 days post-injection |
|---|---|---|---|---|
| *p53-mutant (P279R) B-cells; no pre-selection, no sorting* | | | | |
| p53 (R175H) | 75/25 | 6 | 0.3 +/-0.2 | 51% +/- 18% |

Human p53 does not induce a non-specific immune response

SEQUENCE LISTING

```
<160> NUMBER OF SEQ ID NOS: 10

<210> SEQ ID NO 1
<211> LENGTH: 1432
<212> TYPE: DNA
<213> ORGANISM: Homo sapiens

<400> SEQUENCE: 1
cctccatccg ccccgtctct cccttgaac ctcctcgttc gaccccgcct cgatcctccc      60
tttatccagc cctcactcct tctctaggcg ccggaattcc tgcagcccgg ggggtccatg     120
gaggagccgc agtcagatcc tagcgtcgag ccccctctga gtcaggaaac attttcagac    180
ctatggaaac tacttcctga aaacaacgtt ctgtccccct tgccgtccca agcaatggat    240
gatttgatgc tgtccccgga cgatattgaa caatggttca ctgaagaccc aggtccagat    300
gaagctccca gaatgccaga ggctgctccc cgcgtggccc ctgcaccagc agctcctaca    360
ccggcggccc ctgcaccagc cccctcctgg ccctgtcat cttctgtccc ttcccagaaa     420
acctaccagg gcagctacgg tttccgtctg ggcttcttgc attctgggac agccaagtct    480
```

-continued

```
gtgacttgca cgtactcccc tgccctcaac aagatgtttt gccaactggc caagacctgc    540
cctgtgcagc tgtgggttga ttccacaccc ccgcccggca cccgcgtccg cgccatggcc    600
atctacaagc agtcacagca catgacggag gttgtgaggc gctgccccca ccatgagcgc    660
tgctcagata gcgatggtct ggcccctcct cagcatctta tccgagtgga aggaaatttg    720
cgtgtggagt atttggatga cagaaacact tttcgacata gtgtggtggt gccctatgag    780
ccgcctgagg ttggctctga ctgtaccacc atccactaca actacatgtg taacagttcc    840
tgcatgggcg gcatgaaccg gaggcccatc ctcaccatca tcactggaa agactccagt    900 ggtaatctac tgggacggaa cagctttgag gtgcgtgttt gtgcctgtcc tgggagagac    960
cggcgcacag aggaagagaa tctccgcaag aaagggggagc ctcaccacga gctgccccca    1020
gggagcacta agcgagcact gcccaacaac accagctcct ctccccagcc aaagaagaaa    1080
ccactggatg gagaatattt caccttcag atccgtgggc gtgagcgctt cgagatgttc    1140
cgagagctga atgaggcctt ggaactcaag gatgcccagg ctgggaagga gccaggggg    1200 agcagggctc actccagcca cctgaagtcc aaaaggggtc agtctacctc ccgccataaa    1260
aaactcatgt tcaagacaga agggcctgac tcagatctaa gccgaaaggg ccaggaacgc    1320
ttcaaccgct ggttcctgac gggcatgact gtggccggcg tggttctgct gggctcactc    1380
ttcagtcgga aatgagcggc cgctttacgg ttcctggcct tttgctggag ac            1432
```

<210> SEQ ID NO 2
<211> LENGTH: 425
<212> TYPE: PRT
<213> ORGANISM: Homo sapiens

<400> SEQUENCE: 2

```
Met Glu Glu Pro Gln Ser Asp Pro Ser Val Glu Pro Pro Leu Ser Gln
  1               5                  10                  15

Glu Thr Phe Ser Asp Leu Trp Lys Leu Leu Pro Glu Asn Asn Val Leu
             20                  25                  30

Ser Pro Leu Pro Ser Gln Ala Met Asp Asp Leu Met Leu Ser Pro Asp
         35                  40                  45

Asp Ile Glu Gln Trp Phe Thr Glu Asp Pro Gly Pro Asp Glu Ala Pro
     50                  55                  60

Arg Met Pro Glu Ala Ala Pro Arg Val Ala Pro Ala Pro Ala Ala Pro
 65                  70                  75                  80

Thr Pro Ala Ala Pro Ala Pro Ala Pro Ser Trp Pro Leu Ser Ser Ser
                 85                  90                  95

Val Pro Ser Gln Lys Thr Tyr Gln Gly Ser Tyr Gly Phe Arg Leu Gly
             100                 105                 110

Phe Leu His Ser Gly Thr Ala Lys Ser Val Thr Cys Thr Tyr Ser Pro
         115                 120                 125

Ala Leu Asn Lys Met Phe Cys Gln Leu Ala Lys Thr Cys Pro Val Gln
     130                 135                 140

Leu Trp Val Asp Ser Thr Pro Pro Gly Thr Arg Val Arg Ala Met
145                 150                 155                 160

Ala Ile Tyr Lys Gln Ser Gln His Met Thr Glu Val Val Arg Arg Cys
                 165                 170                 175

Pro His His Glu Arg Cys Ser Asp Ser Asp Gly Leu Ala Pro Pro Gln
             180                 185                 190

His Leu Ile Arg Val Glu Gly Asn Leu Arg Val Glu Tyr Leu Asp Asp
         195                 200                 205
```

```
Arg Asn Thr Phe Arg His Ser Val Val Pro Tyr Glu Pro Pro Glu
    210                 215                 220

Val Gly Ser Asp Cys Thr Thr Ile His Tyr Asn Tyr Met Cys Asn Ser
225                 230                 235                 240

Ser Cys Met Gly Gly Met Asn Arg Arg Pro Ile Leu Thr Ile Ile Thr
                245                 250                 255

Leu Glu Asp Ser Ser Gly Asn Leu Leu Gly Arg Asn Ser Phe Glu Val
                260                 265                 270

Arg Val Cys Ala Cys Pro Gly Arg Asp Arg Arg Thr Glu Glu Glu Asn
            275                 280                 285

Leu Arg Lys Lys Gly Glu Pro His His Glu Leu Pro Pro Gly Ser Thr
    290                 295                 300

Lys Arg Ala Leu Pro Asn Asn Thr Ser Ser Ser Pro Gln Pro Lys Lys
305                 310                 315                 320

Lys Pro Leu Asp Gly Glu Tyr Phe Thr Leu Gln Ile Arg Gly Arg Glu
                325                 330                 335

Arg Phe Glu Met Phe Arg Glu Leu Asn Glu Ala Leu Glu Leu Lys Asp
                340                 345                 350

Ala Gln Ala Gly Lys Glu Pro Gly Gly Ser Arg Ala His Ser Ser His
            355                 360                 365

Leu Lys Ser Lys Lys Gly Gln Ser Thr Ser Arg His Lys Lys Leu Met
    370                 375                 380

Phe Lys Thr Glu Gly Pro Asp Ser Asp Leu Ser Arg Lys Gly Gln Glu
385                 390                 395                 400

Arg Phe Asn Arg Trp Phe Leu Thr Gly Met Thr Val Ala Gly Val Val
                405                 410                 415

Leu Leu Gly Ser Leu Phe Ser Arg Lys
            420                 425

<210> SEQ ID NO 3
<211> LENGTH: 2451
<212> TYPE: DNA
<213> ORGANISM: Homo sapiens

<400> SEQUENCE: 3
cgtgctttcc acgacggtga cacgcttccc tggattggcc agactgcctt ccgggtcact      60
gccatggagg agccgcagtc agatcctagc gtcgagcccc tctgagtca ggaaacattt      120 tcagacctat ggaaactact tcctgaaaac aacgttctgt ccccccttgcc gtcccaagca      180 atggatgatt tgatgctgtc cccggacgat attgaacaat ggttcactga agacccaggt      240
ccagatgaag ctcccagaat gccagaggct gctccccgcg tggcccctgc accagcagct      300
cctacaccgg cggcccctgc accagccccc tcctggcccc tgtcatcttc tgtcccttcc      360
cagaaaacct accagggcag ctacggtttc cgtctgggct tcttgcattc tgggacagcc      420
aagtctgtga cttgcacgta ctcccctgcc ctcaacaaga tgttttgcca actggccaag      480
acctgccctg tgcagctgtg ggttgattcc acaccccgc ccggcacccg tccgcgcc       540 atggccatct acaagcagtc acagcacatg acggaggttg tgaggcgctg ccccccaccat      600 gagcgctgct cagatagcga tggtctggcc cctcctcagc atcttatccg agtggaagga      660
aatttgcgtg tggagtattt ggatgacaga aacacttttc gacatagtgt ggtggtgccc      720
tatgagccgc tgaggttgg ctctgactgt accaccatcc actacaacta catgtgtaac      780
agttcctgca tggcggcat gaaccggagg cccatcctca ccatcatcac actgaagac       840 tccagtggta atctactggg acggaacagc tttgaggtgc atgtttgtgc ctgtcctggg      900
```

-continued

```
agagaccggc gcacagagga agagaatctc cgcaagaaag gggagcctca ccacgagctg    960
cccccaggga gcactaagcg agcactgtcc aacaacacca gctcctctcc ccagccaaag   1020
aagaaaccac tggatggaga atatttcacc cttcagatcc gtgggcgtga gcgcttcgag   1080
atgttccgag agctgaatga ggccttggaa ctcaaggatg cccaggctgg aaggagcca   1140 gggggagca gggctcactc cagccacctg aagtccaaaa agggtcagtc tacctcccgc   1200
cataaaaaac tcatgttcaa gacagaaggg cctgactcag actgacattc tccacttctt   1260
gttccccact gacagcctcc cacccccatc tctccctccc ctgccatttt gggttttggg   1320
tctttgaacc cttgcttgca ataggtgtgc gtcagaagca cccaggactt ccatttgctt   1380
tgtcccgggg ctccactgaa caagttggcc tgcactggtg ttttgttgtg gggaggagga   1440
tggggagtag gacataccag cttagatttt aaggttttta ctgtgaggga tgtttgggag   1500
atgtaagaaa tgttcttgca gttaagggtt agtttacaat cagccacatt ctaggtaggg   1560
gcccacttca ccgtactaac cagggaagct gtccctcact gttgaatttt ctctaacttc   1620
aaggcccata tctgtgaaat gctggcattt gcacctacct cacagagtgc attgtgaggg   1680
ttaatgaaat aatgtacatc tggccttgaa accacctttt attacatggg gtctagaact   1740
tgaccccctt gagggtgctt gttccctctc cctgttggtc ggtgggttgg tagtttctac   1800
agttgggcag ctggttaggt agaggagtt gtcaagtctc tgctggccca gccaaaccct   1860
gtctgacaac ctcttggtga accttagtac ctaaaggaa atctcacccc atcccacacc   1920
ctggaggatt tcatctcttg tatatgatga tctggatcca ccaagacttg ttttatgctc   1980
agggtcaatt tcttttttct ttttttttt tttttctttt ttctttgaga ctgggtctcg   2040 cttttgttgcc caggctggag tggagtggcg tgatcttggc ttactgcagc ctttgcctcc   2100
ccggctcgag cagtcctgcc tcagcctccg gagtagctgg gaccacaggt tcatgccacc   2160
atggccagcc aacttttgca tgttttgtag agatggggtc tcacagtgtt gcccaggctg   2220
gtctcaaact cctgggctca ggcgatccac ctgtctcagc ctcccagagt gctgggatta   2280
caattgtgag ccaccacgtc cagctggaag ggtcaacatc ttttacattc tgcaagcaca   2340
tctgcatttt caccccaccc ttcccctcct tctccctttt tatatcccat ttttatatcg   2400
atctcttatt ttacaataaa actttgctgc caaaaaaaa aaaaaaaaa a              2451
```

<210> SEQ ID NO 4
<211> LENGTH: 720
<212> TYPE: DNA
<213> ORGANISM: Homo sapiens

<400> SEQUENCE: 4

```
atggcgcacg ctgggagaac agggtacgat aaccgggaga tagtgatgaa gtacatccat     60
tataagctgt cgcagagggg ctacgagtgg gatgcgggag atgtgggcgc cgcgcccccg    120
ggggccgccc ccgcgccggg catcttctcc tcgcagcccg ggcacacgcc ccatacagcc    180
gcatcccggg accggtcgc caggacctcg ccgctgcaga ccccggctgc ccccggcgcc    240 gccgcgggc ctgcgctcag cccggtgcca cctgtggtcc acctgaccct ccgccaggcc    300
ggcgacgact tctcccgccg ctaccgccgc gacttcgccg agatgtccag gcagctgcac    360
ctgacgccct tcaccgcgcg gggacgcttt gccacgtgtt tggaggagct cttcagggac    420 gggggtgaact gggggaggat tgtggccttc tttgagttcg gtggggtcat gtgtgtggag    480
agcgtcaacc gggagatgtc gcccctggtg gacaacatcg ccctgtggat gactgagtac    540
```

```
ctgaaccggc acctgcacac ctggatccag gataacggag gctgggatgc ctttgtggaa    600
ctgtacggcc ccagcatgcg gcctctgttt gatttctcct ggctgtctct gaagactctg    660
ctcagtttgg ccctggtggg agcttgcatc accctgggtg cctatctggg ccacaagtga    720
```

<210> SEQ ID NO 5
<211> LENGTH: 702
<212> TYPE: DNA
<213> ORGANISM: Homo sapiens

<400> SEQUENCE: 5

```
atgtctcaga gcaaccggga gctggtggtt gactttctct cctacaagct ttcccagaaa     60
ggatacagct ggagtcagtt tagtgatgtg aagagaaca ggactgaggc cccagaaggg    120
actgaatcgg agatggagac ccccagtgcc atcaatggca acccatcctg gcacctggca    180
gacagccccg cggtgaatgg agccactggc cacagcagca gtttggatgc ccgggaggtg    240
atccccatgg cagcagtaaa gcaagcgctg agggaggcag cgacgagtt tgaactgcgg    300 taccggcggg cattcagtga cctgacatcc cagctccaca tcacccccagg gacagcatat    360 cagagctttg aacaggtagt gaatgaactc ttccgggatg gggtaaactg gggtcgcatt    420 gtggccttttt tctccttcgg cggggcactg tgcgtggaaa gcgtagacaa ggagatgcag    480
gtattggtga gtcggatcgc agcttggatg gccacttacc tgaatgacca cctagagcct    540
tggatccagg agaacggcgg ctgggatact tttgtggaac tctatgggaa caatgcagca    600
gccgagagcc gaaagggcca ggaacgcttc aaccgctggt tcctgacggg catgactgtg    660
gccggcgtgg ttctgctggg ctcactcttc agtcggaaat ga                        702
```

<210> SEQ ID NO 6
<211> LENGTH: 393
<212> TYPE: PRT
<213> ORGANISM: Homo sapiens

<400> SEQUENCE: 6

```
Met Glu Glu Pro Gln Ser Asp Pro Ser Val Glu Pro Pro Leu Ser Gln
1               5                   10                  15

Glu Thr Phe Ser Asp Leu Trp Lys Leu Leu Pro Glu Asn Asn Val Leu
            20                  25                  30

Ser Pro Leu Pro Ser Gln Ala Met Asp Asp Leu Met Leu Ser Pro Asp
        35                  40                  45

Asp Ile Glu Gln Trp Phe Thr Glu Asp Pro Gly Pro Asp Glu Ala Pro
    50                  55                  60

Arg Met Pro Glu Ala Ala Pro Arg Val Ala Pro Ala Pro Ala Ala Pro
65                  70                  75                  80

Thr Pro Ala Ala Pro Ala Pro Ala Pro Ser Trp Pro Leu Ser Ser Ser
                85                  90                  95

Val Pro Ser Gln Lys Thr Tyr Gln Gly Ser Tyr Gly Phe Arg Leu Gly
                100                 105                 110

Phe Leu His Ser Gly Thr Ala Lys Ser Val Thr Cys Thr Tyr Ser Pro
            115                 120                 125

Ala Leu Asn Lys Met Phe Cys Gln Leu Ala Lys Thr Cys Pro Val Gln
        130                 135                 140

Leu Trp Val Asp Ser Thr Pro Pro Pro Gly Thr Arg Val Arg Ala Met
145                 150                 155                 160

Ala Ile Tyr Lys Gln Ser Gln His Met Thr Glu Val Val Arg Arg Cys
                165                 170                 175
```

```
Pro His His Glu Arg Cys Ser Asp Ser Asp Gly Leu Ala Pro Pro Gln
            180                 185                 190

His Leu Ile Arg Val Glu Gly Asn Leu Arg Val Glu Tyr Leu Asp Asp
        195                 200                 205

Arg Asn Thr Phe Arg His Ser Val Val Pro Tyr Glu Pro Pro Glu
    210                 215                 220

Val Gly Ser Asp Cys Thr Thr Ile His Tyr Asn Tyr Met Cys Asn Ser
225                 230                 235                 240

Ser Cys Met Gly Gly Met Asn Arg Arg Pro Ile Leu Thr Ile Ile Thr
                245                 250                 255

Leu Glu Asp Ser Ser Gly Asn Leu Leu Gly Arg Asn Ser Phe Glu Val
            260                 265                 270

Arg Val Cys Ala Cys Pro Gly Arg Asp Arg Arg Thr Glu Glu Glu Asn
        275                 280                 285

Leu Arg Lys Lys Gly Glu Pro His His Glu Leu Pro Pro Gly Ser Thr
    290                 295                 300

Lys Arg Ala Leu Pro Asn Asn Thr Ser Ser Ser Pro Gln Pro Lys Lys
305                 310                 315                 320

Lys Pro Leu Asp Gly Glu Tyr Phe Thr Leu Gln Ile Arg Gly Arg Glu
                325                 330                 335

Arg Phe Glu Met Phe Arg Glu Leu Asn Glu Ala Leu Glu Leu Lys Asp
            340                 345                 350

Ala Gln Ala Gly Lys Glu Pro Gly Gly Ser Arg Ala His Ser Ser His
        355                 360                 365

Leu Lys Ser Lys Lys Gly Gln Ser Thr Ser Arg His Lys Lys Leu Met
    370                 375                 380

Phe Lys Thr Glu Gly Pro Asp Ser Asp
385                 390

<210> SEQ ID NO 7
<211> LENGTH: 233
<212> TYPE: PRT
<213> ORGANISM: Homo sapiens

<400> SEQUENCE: 7

Met Ser Gln Ser Asn Arg Glu Leu Val Val Asp Phe Leu Ser Tyr Lys
1               5                   10                  15

Leu Ser Gln Lys Gly Tyr Ser Trp Ser Gln Phe Ser Asp Val Glu Glu
            20                  25                  30

Asn Arg Thr Glu Ala Pro Glu Gly Thr Glu Ser Glu Met Glu Thr Pro
        35                  40                  45

Ser Ala Ile Asn Gly Asn Pro Ser Trp His Leu Ala Asp Ser Pro Ala
    50                  55                  60

Val Asn Gly Ala Thr Gly His Ser Ser Ser Leu Asp Ala Arg Glu Val
65                  70                  75                  80

Ile Pro Met Ala Ala Val Lys Gln Ala Leu Arg Glu Ala Gly Asp Glu
                85                  90                  95

Phe Glu Leu Arg Tyr Arg Arg Ala Phe Ser Asp Leu Thr Ser Gln Leu
            100                 105                 110

His Ile Thr Pro Gly Thr Ala Tyr Gln Ser Phe Glu Gln Val Val Asn
        115                 120                 125

Glu Leu Phe Arg Asp Gly Val Asn Trp Gly Arg Ile Val Ala Phe Phe
    130                 135                 140

Ser Phe Gly Gly Ala Leu Cys Val Glu Ser Val Asp Lys Glu Met Gln
145                 150                 155                 160
```

-continued

Val Leu Val Ser Arg Ile Ala Ala Trp Met Ala Thr Tyr Leu Asn Asp
            165                 170                 175

His Leu Glu Pro Trp Ile Gln Glu Asn Gly Gly Trp Asp Thr Phe Val
        180                 185                 190

Glu Leu Tyr Gly Asn Asn Ala Ala Glu Ser Arg Lys Gly Gln Glu
        195                 200                 205

Arg Phe Asn Arg Trp Phe Leu Thr Gly Met Thr Val Ala Gly Val Val
    210                 215                 220

Leu Leu Gly Ser Leu Phe Ser Arg Lys
225                 230

<210> SEQ ID NO 8
<211> LENGTH: 239
<212> TYPE: PRT
<213> ORGANISM: Homo sapiens

<400> SEQUENCE: 8

Met Ala His Ala Gly Arg Thr Gly Tyr Asp Asn Arg Glu Ile Val Met
1               5                   10                  15

Lys Tyr Ile His Tyr Lys Leu Ser Gln Arg Gly Tyr Glu Trp Asp Ala
            20                  25                  30

Gly Asp Val Gly Ala Ala Pro Pro Gly Ala Ala Pro Ala Pro Gly Ile
        35                  40                  45

Phe Ser Ser Gln Pro Gly His Thr Pro His Thr Ala Ala Ser Arg Asp
    50                  55                  60

Pro Val Ala Arg Thr Ser Pro Leu Gln Thr Pro Ala Ala Pro Gly Ala
65                  70                  75                  80

Ala Ala Gly Pro Ala Leu Ser Pro Val Pro Pro Val Val His Leu Thr
                85                  90                  95

Leu Arg Gln Ala Gly Asp Asp Phe Ser Arg Arg Tyr Arg Arg Asp Phe
            100                 105                 110

Ala Glu Met Ser Arg Gln Leu His Leu Thr Pro Phe Thr Ala Arg Gly
        115                 120                 125

Arg Phe Ala Thr Val Val Glu Glu Leu Phe Arg Asp Gly Val Asn Trp
    130                 135                 140

Gly Arg Ile Val Ala Phe Phe Glu Phe Gly Gly Val Met Cys Val Glu
145                 150                 155                 160

Ser Val Asn Arg Glu Met Ser Pro Leu Val Asp Asn Ile Ala Leu Trp
                165                 170                 175

Met Thr Glu Tyr Leu Asn Arg His Leu His Thr Trp Ile Gln Asp Asn
            180                 185                 190

Gly Gly Trp Asp Ala Phe Val Glu Leu Tyr Gly Pro Ser Met Arg Pro
        195                 200                 205

Leu Phe Asp Phe Ser Trp Leu Ser Leu Lys Thr Leu Leu Ser Leu Ala
    210                 215                 220

Leu Val Gly Ala Cys Ile Thr Leu Gly Ala Tyr Leu Gly His Lys
225                 230                 235

<210> SEQ ID NO 9
<211> LENGTH: 32
<212> TYPE: PRT
<213> ORGANISM: Homo sapiens

<400> SEQUENCE: 9

Leu Ser Arg Lys Gly Gln Glu Arg Phe Asn Arg Trp Phe Leu Thr Gly
1               5                   10                  15

```
Met Thr Val Ala Gly Val Val Leu Leu Gly Ser Leu Phe Ser Arg Lys
            20                  25                  30
```

<210> SEQ ID NO 10
<211> LENGTH: 1278
<212> TYPE: DNA
<213> ORGANISM: Homo sapiens

<400> SEQUENCE: 10

```
atggaggagc cgcagtcaga tcctagcgtc gagcccctc  tgagtcagga aacattttca      60
gacctatgga aactacttcc tgaaaacaac gttctgtccc ccttgccgtc ccaagcaatg     120
gatgatttga tgctgtcccc ggacgatatt gaacaatggt tcactgaaga cccaggtcca     180
gatgaagctc ccagaatgcc agaggctgct ccccgcgtgg ccoctgcacc agcagctcct     240
acaccggcgg ccoctgcacc agcccoctcc tggcccctgt catcttctgt cccttcccag     300
aaaacctacc agggcagcta cggtttccgt ctgggcttct tgcattctgg gacagccaag     360
tctgtgactt gcacgtactc ccotgccctc aacaagatgt tttgccaact ggccaagacc     420
tgccctgtgc agctgtgggt tgattccaca ccccgcccg  gcacccgcgt ccgcgccatg     480
gccatctaca agcagtcaca gcacatgacg gaggttgtga ggcgctgccc ccaccatgag     540
cgctgctcag atagcgatgg tctggcccct cctcagcatc ttatccgagt ggaaggaaat     600
ttgcgtgtgg agtatttgga tgacagaaac acttttcgac atagtgtggt ggtgccctat     660
gagccgcctg aggttggctc tgactgtacc accatccact acaactacat gtgtaacagt     720
tcctgcatgg gcggcatgaa ccggaggccc atcctcacca tcatcacact ggaagactcc     780
agtggtaatc tactgggacg gaacagcttt gaggtgcgtg tttgtgcctg tcctgggaga     840
gaccggcgca cagaggaaga gaatctccgc aagaaagggg agcctcacca cgagctgccc     900
ccagggagca ctaagcgagc actgcccaac aacaccagct cctctcccca gccaaagaag     960
aaaccactgg atggagaata tttcaccctt cagatccgtg ggcgtgagcg cttcgagatg    1020
ttccgagagc tgaatgaggc cttggaactc aaggatgccc aggctgggaa ggagccaggg    1080
gggagcaggg ctcactccag ccacctgaag tccaaaaagg gtcagtctac ctcccgccat    1140
aaaaaactca tgttcaagac agaagggcct gactcagatc taagccgaaa gggccaggaa    1200
cgcttcaacc gctggttcct gacgggcatg actgtggccg gcgtggttct gctgggctca    1260
ctcttcagtc ggaaatga                                                  1278
```

US 7,271,001 B2

METHOD FOR MITOCHONDRIAL TARGETING OF P53

This invention was made with government support under Grant No. 2RO1CA6066410A1 awarded by the National Cancer Institute. The Government has certain rights in the invention.

FIELD OF THE INVENTION

The present invention relates to methods and compositions for modulating apoptotic pathways. In particular, the present invention relates to methods and compositions for inducing apoptosis in cancer cells. The present invention further relates to methods and compositions for identifying drugs that modulate apoptotic pathways.

BACKGROUND OF THE INVENTION

The term cancer collectively refers to more than 100 different diseases that affect nearly every part of the body. Throughout life, healthy cells in the body divide, grow, and replace themselves in a controlled fashion. Cancer starts when the genes directing this cellular division malfunction, and cells begin to multiply and grow out of control. A mass or clump of these abnormal cells is called a tumor. Not all tumors are cancerous. Benign tumors, such as moles, stop growing and do not spread to other parts of the body. But cancerous, or malignant, tumors continue to grow, crowding out healthy cells, interfering with body functions, and drawing nutrients away from body tissues. Malignant tumors can spread to other parts of the body through a process called metastasis. Cells from the original tumor break off, travel through the blood or lymphatic vessels or within the chest, abdomen or pelvis, depending on the tumor, and eventually form new tumors elsewhere in the body.

Only 5-10% of cancers are thought to be hereditary. The rest of the time, the genetic mutation that leads to the disease is brought on by other factors. The most common cancers are linked to smoking, sun exposure, and diet. These factors, combined with age, family history, and overall health, contribute to an individual's cancer risk.

Current treatments for cancer include drug therapy (chemotherapy), radiation, and hormonal therapy. While new therapies have improved cancer survival rates, improved therapies, specifically those that target cancer cells but not healthy cells, are still needed.

SUMMARY OF THE INVENTION

The present invention relates to methods and compositions for modulating apoptotic pathways. In particular, the present invention relates to methods and compositions for inducing apoptosis in cancer cells. The present invention further relates to methods and compositions for identifying drugs that modulate apoptotic pathways.

Accordingly, in some embodiments, the present invention provides a method, comprising providing a cell, wherein the cell lacks functional mitochondrial p53; and delivering exogenous p53 in the cell, wherein the p53 comprises a sequence that directs the p53 to the mitochondria of the cell. In some embodiments, the exogenous p53 is at least 90% identical to SEQ ID NO:3. In other embodiments, the exogenous p53 has the nucleic acid sequence of SEQ ID NO:3. In some embodiments, the exogenous p53 is operably linked to a mitochondrial targeting molecule. In certain embodiments, the exogenous p53 is operably linked to a Bcl2 mitochondria targeting sequence (e.g., SEQ ID NO: 4). In other embodiments, the exogenous p53 is operably linked to a BclXL mitochondrial targeting sequence (e.g., SEQ ID NO:5). In some embodiments, the exogenous p53 and the mitochondrial targeting molecule are in a vector (e.g., comprising the nucleic acid sequence of SEQ ID NO:1). In some embodiments, the delivering comprises delivering the vector to the cell. In some embodiments, the vector encodes a fusion protein having the amino acid sequence of SEQ ID NO:2. In some embodiments, the delivering results in apoptosis of the cell. In some embodiments, the method further comprising delivering a second exogenous p53 to the nucleus of said cell. In some embodiments, the second exogenous p53 is contained in a second vector comprising a second sequence that directs the second exogenous p53 to the nucleus of the cell.

In certain embodiments, the cell is in a host animal (e.g., a non-human mammal or a human). In some embodiments, the host animal has been diagnosed with cancer and the cell is a cancer cell. In some preferred embodiments, the delivering results in apoptosis of the cancer cell. In other embodiments, the host animal has been diagnosed with an autoimmune disease. In certain further embodiments, the method further comprises the step of delivering a test compound to the host animal. In other embodiments, the cell is in vitro. In some embodiments, the method further comprises the step of delivering a test compound to the cell.

The present invention further provides a composition comprising a nucleic acid comprising an exogenous p53 gene operably linked to a gene encoding a mitochondrial targeting protein. In some embodiments, the exogenous p53 is at least 90% identical to SEQ ID NO:3. In other embodiments, the exogenous p53 has the nucleic acid sequence of SEQ ID NO:3. In certain embodiments, the exogenous p53 is operably linked to a Bcl2 mitochondria targeting sequence (e.g., SEQ ID NO: 4). In other embodiments, the exogenous p53 is operably linked to a BclXL mitochondrial targeting sequence (e.g., SEQ ID NO:5). In some embodiments, the nucleic acid has the sequence of SEQ ID NO:1. In some embodiments, the nucleic acid encodes a fusion protein having the amino acid sequence of SEQ ID NO:2.

In still further embodiments, the present invention provides a vector encoding the nucleic acid sequence. In some embodiments, the present invention further provides a second vector, wherein the second vector comprises a second exogenous p53 and a sequence that targets the second p53 to the nucleus of a cell. In yet other embodiments, the present invention provides a kit comprising the vector and instructions for using the vector for inducing apoptosis in a cell.

DESCRIPTION OF THE FIGURES

FIG. 1 shows an overview of the transplantable Eµ myc B-lymphoma model.

FIG. 2 shows characterization of lymphoma isolates used in subsequent in vivo studies. FIG. 2a shows various naturally occurring genotypes of B-lymphoma isolates generated from Eµ myc transgenic mice. FIG. 2b shows that mitochondrially targeted p53 protein levels achieved by vector delivery are similar to physiological stress-induced levels. FIG. 2c shows retrovirally driven expression of nuclear and mitochondrially targeted p53 in NIH3T3 cells detected by immunoblot. FIG. 2d shows viral transduction efficiencies, as determined by co-expressed GFP marker via FACS analysis 36 hours after transduction.

3a shows that mitochondrial p53 promotes apoptosis in MEFs.

FIG. 4 show functional characterization of mitochondrially targeted p53 in p53 null lymphoma cells in vitro. FIGS. 4a and 4b show that mitochondrially targeted p53 restrains growth in culture.

FIG. 5 shows that mitochondrially targeted p53 kills lymphoma cells in vivo. FIG. 5 shows representative examples of FACS analyses of residual GFP expression in reconstituted lymphomas harvested at day 28.

FIG. 9 shows the nucleic acid sequence of p53CTB (SEQ ID NO:1). Letters in bold correspond to the BclXL-derived sequence.

FIG. 10 shows the amino acid (SEQ ID NO:2) and nucleotide (SEQ ID NO:10) sequences of p53CTB.

FIG. 11 shows Table 1.

FIG. 12 shows Table 2.

FIG. 13 shows the amino acid sequences of human p53 (SEQ ID NO:6); human BclXL (SEQ ID NO:7); and human Bcl2 (SEQ ID NO:8).

FIG. 14 shows the nucleic acid sequences of human p53 (SEQ ID NO:3); human BclXL (SEQ ID NO:5); and human Bcl2 (SEQ ID NO:4).

FIG. 15 shows Table 3.

DEFINITIONS

Figure 3A:
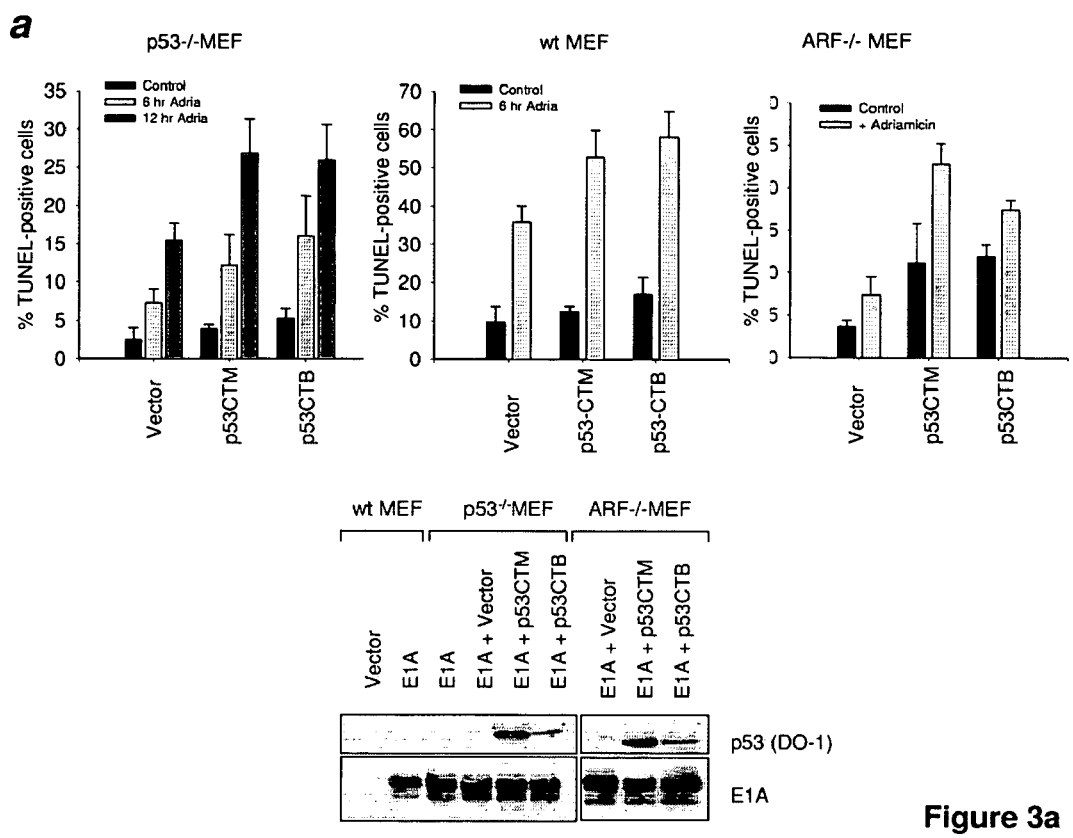
FIG. 3 shows functional characterization of mitochondrially targeted p53 in primary mouse embryo fibroblasts. FIG.
FIG. 3b shows that mitochondrially targeted p53 proteins lack transcriptional activity.

To facilitate an understanding of the present invention, a number of terms and phrases are defined below:

As used herein, the term "subject" refers to any animal (e.g., a mammal), including, but not limited to, humans, non-human primates, rodents, and the like, which is to be the recipient of a particular treatment. Typically, the terms "subject" and "patient" are used interchangeably herein in reference to a human subject.

As used herein, the term "subject diagnosed with a cancer" refers to a subject who has been tested and found to have cancerous cells. The cancer may be diagnosed using any suitable method, including but not limited to, biopsy, x-ray, blood test, and the diagnostic methods of the present invention.

As used herein, the term "detecting a decrease in viability" refers to a decrease in the number of living cells in a culture. In preferred embodiments, the decrease is due to the induction of programmed cell death (e.g., apoptosis) in some or all of the cells in a population.

As used herein, the term "induces cell death" refers to a molecule (e.g., a p53 targeting vector of the present invention, a test compound or a drug) that induces a programmed cell death (e.g., apoptosis).

As used herein, the term "stage of cancer" refers to a qualitative or quantitative assessment of the level of advancement of a cancer. Criteria used to determine the stage of a cancer include, but are not limited to, the size of the tumor, whether the tumor has spread to other parts of the body and where the cancer has spread (e.g., within the same organ or region of the body or to another organ).

As used herein, the term "non-human animals" refers to all non-human animals including, but not limited to, vertebrates such as rodents, non-human primates, ovines, bovines, ruminants, lagomorphs, porcines, caprines, equines, canines, felines, aves, etc.

As used herein, the term "gene transfer system" refers to any means of delivering a composition comprising a nucleic acid sequence to a cell or tissue. For example, gene transfer systems include, but are not limited to, vectors (e.g., retroviral, adenoviral, adeno-associated viral, and other nucleic acid-based delivery systems), microinjection of naked nucleic acid, polymer-based delivery systems (e.g., liposome-based and metallic particle-based systems), biolistic injection, and the like. As used herein, the term "viral gene transfer system" refers to gene transfer systems comprising viral elements (e.g., intact viruses, modified viruses and viral components such as nucleic acids or proteins) to facilitate delivery of the sample to a desired cell or tissue. As used herein, the term "adenovirus gene transfer system" refers to gene transfer systems comprising intact or altered viruses belonging to the family Adenoviridae.

As used herein, the term "site-specific recombination target sequences" refers to nucleic acid sequences that provide recognition sequences for recombination factors and the location where recombination takes place.

As used herein, the term "nucleic acid molecule" refers to any nucleic acid containing molecule, including but not limited to, DNA or RNA. The term encompasses sequences that include any of the known base analogs of DNA and RNA including, but not limited to, 4-acetylcytosine, 8-hydroxy-N-6-methyladenosine, aziridinylcytosine, pseudoisocytosine, 5-(carboxyhydroxylmethyl)uracil, 5-fluorouracil, 5-bromouracil, 5-carboxymethylaminomethyl-2-thiouracil, 5-carboxymethylaminomethyluracil, dihydrouracil, inosine, N6-isopentenyladenine, 1-methyladenine, 1-methylpseudouracil, 1-methylguanine, 1-methylinosine, 2,2-dimethylguanine, 2-methyladenine, 2-methylguanine, 3-methylcytosine, 5-methylcytosine, N6-methyladenine, 7-methylguanine, 5-methylaminomethyluracil, 5-methoxyaminomethyl-2-thiouracil, beta-D-mannosylqueosine, 5'-methoxycarbonylmethyluracil, 5-methoxyuracil, 2-methylthio-N-6-isopentenyladenine, uracil-5-oxyacetic acid methylester, uracil-5-oxyacetic acid, oxybutoxosine, pseudouracil, queosine, 2-thiocytosine, 5-methyl-2-thiouracil, 2-thiouracil, 4-thiouracil, 5-methyluracil, N-uracil-5-oxyacetic acid methylester, uracil-5-oxyacetic acid, pseudouracil, queosine, 2-thiocytosine, and 2,6-diaminopurine.

The term "gene" refers to a nucleic acid (e.g., DNA) sequence that comprises coding sequences necessary for the production of a polypeptide, precursor, or RNA (e.g., rRNA, tRNA). The polypeptide can be encoded by a full length coding sequence or by any portion of the coding sequence so long as the desired activity or functional properties (e.g., enzymatic activity, ligand binding, signal transduction, immunogenicity, etc.) of the full-length or fragment are retained. The term also encompasses the coding region of a structural gene and the sequences located adjacent to the coding region on both the 5' and 3' ends for a distance of about 1 kb or more on either end such that the gene corresponds to the length of the full-length mRNA. Sequences located 5' of the coding region and present on the mRNA are referred to as 5' non-translated sequences.

Sequences located 3' or downstream of the coding region and present on the mRNA are referred to as 3' non-translated sequences. The term "gene" encompasses both cDNA and genomic forms of a gene. A genomic form or clone of a gene contains the coding region interrupted with non-coding sequences termed "introns" or "intervening regions" or "intervening sequences." Introns are segments of a gene that are transcribed into nuclear RNA (hnRNA); introns may contain regulatory elements such as enhancers. Introns are removed or "spliced out" from the nuclear or primary transcript; introns therefore are absent in the messenger RNA (mRNA) transcript. The mRNA functions during translation to specify the sequence or order of amino acids in a nascent polypeptide.

As used herein, the term "heterologous gene" refers to a gene that is not in its natural environment. For example, a heterologous gene includes a gene from one species introduced into another species. A heterologous gene also includes a gene native to an organism that has been altered in some way (e.g., mutated, added in multiple copies, linked to non-native regulatory sequences, etc). Heterologous genes are distinguished from endogenous genes in that the heterologous gene sequences are typically joined to DNA sequences that are not found naturally associated with the gene sequences in the chromosome or are associated with portions of the chromosome not found in nature (e.g., genes expressed in loci where the gene is not normally expressed).

As used herein, the term "transgene" refers to a heterologous gene that is integrated into the genome of an organism (e.g., a non-human animal) and that is transmitted to progeny of the organism during sexual reproduction.

As used herein, the term "transgenic organism" refers to an organism (e.g., a non-human animal) that has a transgene integrated into its genome and that transmits the transgene to its progeny during sexual reproduction.

As used herein, the term "gene expression" refers to the process of converting genetic information encoded in a gene into RNA (e.g., mRNA, rRNA, tRNA, or snRNA) through "transcription" of the gene (i.e., via the enzymatic action of an RNA polymerase), and for protein encoding genes, into protein through "translation" of mRNA. Gene expression can be regulated at many stages in the process. "Up-regulation" or "activation" refers to regulation that increases the production of gene expression products (i.e., RNA or protein), while "down-regulation" or "repression" refers to regulation that decrease production. Molecules (e.g., transcription factors) that are involved in up-regulation or down-regulation are often called "activators" and "repressors," respectively.

In addition to containing introns, genomic forms of a gene may also include sequences located on both the 5' and 3' end of the sequences that are present on the RNA transcript. These sequences are referred to as "flanking" sequences or regions (these flanking sequences are located 5' or 3' to the non-translated sequences present on the mRNA transcript). The 5' flanking region may contain regulatory sequences such as promoters and enhancers that control or influence the transcription of the gene. The 3' flanking region may contain sequences that direct the termination of transcription, post-transcriptional cleavage and polyadenylation.

The term "wild-type" refers to a gene or gene product isolated from a naturally occurring source. A wild-type gene is that which is most frequently observed in a population and is thus arbitrarily designed the "normal" or "wild-type" form of the gene. In contrast, the term "modified" or "mutant" refers to a gene or gene product that displays modifications in sequence and or functional properties (i.e., altered characteristics) when compared to the wild-type gene or gene product. It is noted that naturally occurring mutants can be isolated; these are identified by the fact that they have altered characteristics (including altered nucleic acid sequences) when compared to the wild-type gene or gene product.

As used herein, the terms "nucleic acid molecule encoding," "DNA sequence encoding," and "DNA encoding" refer to the order or sequence of deoxyribonucleotides along a strand of deoxyribonucleic acid. The order of these deoxyribonucleotides determines the order of amino acids along the polypeptide (protein) chain. The DNA sequence thus codes for the amino acid sequence.

As used herein, the terms "an oligonucleotide having a nucleotide sequence encoding a gene" and "polynucleotide having a nucleotide sequence encoding a gene," means a nucleic acid sequence comprising the coding region of a gene or in other words the nucleic acid sequence that encodes a gene product. The coding region may be present in a cDNA, genomic DNA or RNA form. When present in a DNA form, the oligonucleotide or polynucleotide may be single-stranded (i.e., the sense strand) or double-stranded. Suitable control elements such as enhancers/promoters, splice junctions, polyadenylation signals, etc. may be placed in close proximity to the coding region of the gene if needed to permit proper initiation of transcription and/or correct processing of the primary RNA transcript. Alternatively, the coding region utilized in the expression vectors of the present invention may contain endogenous enhancers/promoters, splice junctions, intervening sequences, polyadenylation signals, etc. or a combination of both endogenous and exogenous control elements.

As used herein, the term "oligonucleotide," refers to a short length of single-stranded polynucleotide chain. Oligonucleotides are typically less than 200 residues long (e.g., between 15 and 100), however, as used herein, the term is also intended to encompass longer polynucleotide chains. Oligonucleotides are often referred to by their length. For example a 24 residue oligonucleotide is referred to as a "24-mer". Oligonucleotides can form secondary and tertiary structures by self-hybridizing or by hybridizing to other polynucleotides. Such structures can include, but are not limited to, duplexes, hairpins, cruciforms, bends, and triplexes.

As used herein, the terms "complementary" or "complementarity" are used in reference to polynucleotides (i.e., a sequence of nucleotides) related by the base-pairing rules. For example, for the sequence "A-G-T," is complementary to the sequence "T-C-A." Complementarity may be "partial," in which only some of the nucleic acids' bases are matched according to the base pairing rules. Or, there may be "complete" or "total" complementarity between the nucleic acids. The degree of complementarity between nucleic acid strands has significant effects on the efficiency and strength of hybridization between nucleic acid strands. This is of particular importance in amplification reactions, as well as detection methods that depend upon binding between nucleic acids.

The term "homology" refers to a degree of complementarity. There may be partial homology or complete homology (i.e., identity). A partially complementary sequence is a nucleic acid molecule that at least partially inhibits a completely complementary nucleic acid molecule from hybridizing to a target nucleic acid is "substantially homologous." The inhibition of hybridization of the completely complementary sequence to the target sequence may be examined using a hybridization assay (Southern or Northern blot, solution hybridization and the like) under conditions of low stringency. A substantially homologous sequence or probe will compete for and inhibit the binding (i.e., the hybridization) of a completely homologous nucleic acid molecule to a target under conditions of low stringency. This is not to say that conditions of low stringency are such that non-specific binding is permitted; low stringency conditions require that the binding of two sequences to one another be a specific (i.e., selective) interaction. The absence of non-specific binding may be tested by the use of a second target that is substantially non-complementary (e.g., less than about 30% identity); in the absence of non-specific binding the probe will not hybridize to the second non-complementary target.

When used in reference to a double-stranded nucleic acid sequence such as a cDNA or genomic clone, the term "substantially homologous" refers to any probe that can hybridize to either or both strands of the double-stranded nucleic acid sequence under conditions of low stringency as described above.

A gene may produce multiple RNA species that are generated by differential splicing of the primary RNA transcript. cDNAs that are splice variants of the same gene will contain regions of sequence identity or complete homology (representing the presence of the same exon or portion of the same exon on both cDNAs) and regions of complete non-identity (for example, representing the presence of exon "A" on cDNA 1 wherein cDNA 2 contains exon "B" instead). Because the two cDNAs contain regions of sequence identity they will both hybridize to a probe derived from the entire gene or portions of the gene containing sequences found on both cDNAs; the two splice variants are therefore substantially homologous to such a probe and to each other.

When used in reference to a single-stranded nucleic acid sequence, the term "substantially homologous" refers to any probe that can hybridize (i.e., it is the complement of) the single-stranded nucleic acid sequence under conditions of low stringency as described above.

As used herein, the term "hybridization" is used in reference to the pairing of complementary nucleic acids. Hybridization and the strength of hybridization (i.e., the strength of the association between the nucleic acids) is impacted by such factors as the degree of complementary between the nucleic acids, stringency of the conditions involved, the $T_m$ of the formed hybrid, and the G:C ratio within the nucleic acids. A single molecule that contains pairing of complementary nucleic acids within its structure is said to be "self-hybridized."

As used herein, the term "$T_m$" is used in reference to the "melting temperature." The melting temperature is the temperature at which a population of double-stranded nucleic acid molecules becomes half dissociated into single strands. The equation for calculating the $T_m$ of nucleic acids is well known in the art. As indicated by standard references, a simple estimate of the $T_m$ value may be calculated by the equation: $T_m=81.5+0.41$ (% G+C), when a nucleic acid is in aqueous solution at 1 M NaCl (See e.g., Anderson and Young, Quantitative Filter Hybridization, in Nucleic Acid Hybridization [1985]). Other references include more sophisticated computations that take structural as well as sequence characteristics into account for the calculation of $T_m$.

As used herein the term "stringency" is used in reference to the conditions of temperature, ionic strength, and the presence of other compounds such as organic solvents, under which nucleic acid hybridizations are conducted. Under "low stringency conditions" a nucleic acid sequence of interest will hybridize to its exact complement, sequences with single base mismatches, closely related sequences (e.g., sequences with 90% or greater homology), and sequences having only partial homology (e.g., sequences with 50-90% homology). Under "medium stringency conditions," a nucleic acid sequence of interest will hybridize only to its exact complement, sequences with single base mismatches, and closely relation sequences (e.g., 90% or greater homology). Under "high stringency conditions," a nucleic acid sequence of interest will hybridize only to its exact complement, and (depending on conditions such a temperature) sequences with single base mismatches. In other words, under conditions of high stringency the temperature can be raised so as to exclude hybridization to sequences with single base mismatches.

"High stringency conditions" when used in reference to nucleic acid hybridization comprise conditions equivalent to binding or hybridization at 42° C. in a solution consisting of 5×SSPE (43.8 g/l NaCl, 6.9 g/l $NaH_2PO_4.H_2O$ and 1.85 g/l EDTA, pH adjusted to 7.4 with NaOH), 0.5% SDS, 5× Denhardt's reagent and 100 µg/ml denatured salmon sperm DNA followed by washing in a solution comprising 0.1× SSPE, 1.0% SDS at 42° C. when a probe of about 500 nucleotides in length is employed.

"Medium stringency conditions" when used in reference to nucleic acid hybridization comprise conditions equivalent to binding or hybridization at 42° C. in a solution consisting of 5×SSPE (43.8 g/l NaCl, 6.9 g/l $NaH_2PO_4.H_2O$ and 1.85 g/l EDTA, pH adjusted to 7.4 with NaOH), 0.5% SDS, 5× Denhardt's reagent and 100 µg/ml denatured salmon sperm DNA followed by washing in a solution comprising 1.0× SSPE, 1.0% SDS at 42° C. when a probe of about 500 nucleotides in length is employed.

"Low stringency conditions" comprise conditions equivalent to binding or hybridization at 42° C. in a solution consisting of 5×SSPE (43.8 g/l NaCl, 6.9 g/l $NaH_2PO_4.H_2O$ and 1.85 g/l EDTA, pH adjusted to 7.4 with NaOH), 0.1% SDS, 5× Denhardt's reagent [50× Denhardt's contains per 500 ml: 5 g Ficoll (Type 400, Pharamcia), 5 g BSA (Fraction V; Sigma)] and 100 µg/ml denatured salmon sperm DNA followed by washing in a solution comprising 5×SSPE, 0.1% SDS at 42° C. when a probe of about 500 nucleotides in length is employed.

The art knows well that numerous equivalent conditions may be employed to comprise low stringency conditions; factors such as the length and nature (DNA, RNA, base composition) of the probe and nature of the target (DNA, RNA, base composition, present in solution or immobilized, etc.) and the concentration of the salts and other components (e.g., the presence or absence of formamide, dextran sulfate, polyethylene glycol) are considered and the hybridization solution may be varied to generate conditions of low stringency hybridization different from, but equivalent to, the above listed conditions. In addition, the art knows conditions that promote hybridization under conditions of high stringency (e.g., increasing the temperature of the hybridization and/or wash steps, the use of formamide in the hybridization solution, etc.) (see definition above for "stringency").

As used herein, the terms "restriction endonucleases" and "restriction enzymes" refer to bacterial enzymes, each of which cut double-stranded DNA at or near a specific nucleotide sequence.

The terms "in operable combination," "in operable order," and "operably linked" as used herein refer to the linkage of nucleic acid sequences in such a manner that a nucleic acid molecule capable of directing the transcription of a given gene and/or the synthesis of a desired protein molecule is produced. The term also refers to the linkage of amino acid sequences in such a manner so that a functional protein is produced.

The term "isolated" when used in relation to a nucleic acid, as in "an isolated oligonucleotide" or "isolated polynucleotide" refers to a nucleic acid sequence that is identified and separated from at least one component or contaminant with which it is ordinarily associated in its natural source. Isolated nucleic acid is such present in a form or setting that is different from that in which it is found in nature. In contrast, non-isolated nucleic acids as nucleic acids such as DNA and RNA found in the state they exist in nature. For example, a given DNA sequence (e.g., a gene) is found on the host cell chromosome in proximity to neighboring genes; RNA sequences, such as a specific mRNA sequence encoding a specific protein, are found in the cell as a mixture with numerous other mRNAs that encode a multitude of proteins. However, isolated nucleic acid encoding a given protein includes, by way of example, such nucleic acid in cells ordinarily expressing the given protein where the nucleic acid is in a chromosomal location different from that of natural cells, or is otherwise flanked by a different nucleic acid sequence than that found in nature. The isolated nucleic acid, oligonucleotide, or polynucleotide may be present in single-stranded or double-stranded form. When an isolated nucleic acid, oligonucleotide or polynucleotide is to be utilized to express a protein, the oligonucleotide or polynucleotide will contain at a minimum the sense or coding strand (i.e., the oligonucleotide or polynucleotide may be single-stranded), but may contain both the sense and anti-sense strands (i.e., the oligonucleotide or polynucleotide may be double-stranded).

As used herein, the term "purified" or "to purify" refers to the removal of components (e.g., contaminants) from a sample. For example, antibodies are purified by removal of contaminating non-immunoglobulin proteins; they are also purified by the removal of immunoglobulin that does not bind to the target molecule. The removal of non-immunoglobulin proteins and/or the removal of immunoglobulins that do not bind to the target molecule results in an increase in the percent of target-reactive immunoglobulins in the sample. In another example, recombinant polypeptides are expressed in bacterial host cells and the polypeptides are purified by the removal of host cell proteins; the percent of recombinant polypeptides is thereby increased in the sample.

"Amino acid sequence" and terms such as "polypeptide" or "protein" are not meant to limit the amino acid sequence to the complete, native amino acid sequence associated with the recited protein molecule.

The term "native protein" as used herein to indicate that a protein does not contain amino acid residues encoded by vector sequences; that is, the native protein contains only those amino acids found in the protein as it occurs in nature. A native protein may be produced by recombinant means or may be isolated from a naturally occurring source.

As used herein the term "portion" when in reference to a protein (as in "a portion of a given protein") refers to fragments of that protein. The fragments may range in size from four amino acid residues to the entire amino acid sequence minus one amino acid.

The term "Southern blot," refers to the analysis of DNA on agarose or acrylamide gels to fractionate the DNA according to size followed by transfer of the DNA from the gel to a solid support, such as nitrocellulose or a nylon membrane. The immobilized DNA is then probed with a labeled probe to detect DNA species complementary to the probe used. The DNA may be cleaved with restriction enzymes prior to electrophoresis. Following electrophoresis, the DNA may be partially depurinated and denatured prior to or during transfer to the solid support. Southern blots are a standard tool of molecular biologists (J. Sambrook et al., Molecular Cloning: A Laboratory Manual, Cold Spring Harbor Press, N.Y., pp 9.31-9.58 [1989]).

As used herein, the term "vector" is used in reference to nucleic acid molecules that transfer DNA segment(s) from one cell to another. The term "vehicle" is sometimes used interchangeably with "vector." Vectors are often derived from plasmids, bacteriophages, or plant or animal viruses.

The term "expression vector" as used herein refers to a recombinant DNA molecule containing a desired coding sequence and appropriate nucleic acid sequences necessary for the expression of the operably linked coding sequence in a particular host organism. Nucleic acid sequences necessary for expression in prokaryotes usually include a promoter, an operator (optional), and a ribosome binding site, often along with other sequences. Eukaryotic cells are known to utilize promoters, enhancers, and termination and polyadenylation signals.

The terms "overexpression" and "overexpressing" and grammatical equivalents, are used in reference to levels of mRNA to indicate a level of expression approximately 3-fold higher (or greater) than that observed in a given tissue in a control or non-transgenic animal. Levels of mRNA are measured using any of a number of techniques known to those skilled in the art including, but not limited to Northern blot analysis. Appropriate controls are included on the Northern blot to control for differences in the amount of RNA loaded from each tissue analyzed (e.g., the amount of 28S rRNA, an abundant RNA transcript present at essentially the same amount in all tissues, present in each sample can be used as a means of normalizing or standardizing the mRNA-specific signal observed on Northern blots). The amount of mRNA present in the band corresponding in size to the correctly spliced transgene RNA is quantified; other minor species of RNA which hybridize to the transgene probe are not considered in the quantification of the expression of the transgenic mRNA.

The term "transfection" as used herein refers to the introduction of foreign DNA into eukaryotic cells. Transfection may be accomplished by a variety of means known to the art including calcium phosphate-DNA co-precipitation, DEAE-dextran-mediated transfection, polybrene-mediated transfection, electroporation, microinjection, liposome fusion, lipofection, protoplast fusion, retroviral infection, and biolistics.

The term "calcium phosphate co-precipitation" refers to a technique for the introduction of nucleic acids into a cell. The uptake of nucleic acids by cells is enhanced when the nucleic acid is presented as a calcium phosphate-nucleic acid co-precipitate.

The original technique of Graham and van der Eb (Graham and van der Eb, Virol., 52:456 [1973]), has been modified by several groups to optimize conditions for particular types of cells. The art is well aware of these numerous modifications.

The term "stable transfection" or "stably transfected" refers to the introduction and integration of foreign DNA into the genome of the transfected cell. The term "stable transfectant" refers to a cell that has stably integrated foreign DNA into the genomic DNA.

The term "transient transfection" or "transiently transfected" refers to the introduction of foreign DNA into a cell where the foreign DNA fails to integrate into the genome of the transfected cell. The foreign DNA persists in the nucleus of the transfected cell for several days. During this time the foreign DNA is subject to the regulatory controls that govern the expression of endogenous genes in the chromosomes. The term "transient transfectant" refers to cells that have taken up foreign DNA but have failed to integrate this DNA.

As used herein, the term "selectable marker" refers to the use of a gene that encodes an enzymatic activity that confers the ability to grow in medium lacking what would otherwise be an essential nutrient (e.g. the HIS3 gene in yeast cells); in addition, a selectable marker may confer resistance to an antibiotic or drug upon the cell in which the selectable marker is expressed. Selectable markers may be "dominant"; a dominant selectable marker encodes an enzymatic activity that can be detected in any eukaryotic cell line. Examples of dominant selectable markers include the bacterial aminoglycoside 3' phosphotransferase gene (also referred to as the neo gene) that confers resistance to the drug G418 in mammalian cells, the bacterial hygromycin G phosphotransferase (hyg) gene that confers resistance to the antibiotic hygromycin and the bacterial xanthine-guanine phosphoribosyl transferase gene (also referred to as the gpt gene) that confers the ability to grow in the presence of mycophenolic acid. Other selectable markers are not dominant in that their use must be in conjunction with a cell line that lacks the relevant enzyme activity. Examples of non-dominant selectable markers include the thymidine kinase (tk) gene that is used in conjunction with tk$^-$ cell lines, the CAD gene that is used in conjunction with CAD-deficient cells and the mammalian hypoxanthine-guanine phosphoribosyl transferase (hprt) gene that is used in conjunction with hprt$^-$ cell lines. A review of the use of selectable markers in mammalian cell lines is provided in Sambrook, J. et al., Molecular Cloning: A Laboratory Manual, 2nd ed., Cold Spring Harbor Laboratory Press, New York (1989) pp. 16.9-16.15.

As used herein, the term "cell culture" refers to any in vitro culture of cells. Included within this term are continuous cell lines (e.g., with an immortal phenotype), primary cell cultures, transformed cell lines, finite cell lines (e.g., non-transformed cells), and any other cell population maintained in vitro.

As used, the term "eukaryote" refers to organisms distinguishable from "prokaryotes." It is intended that the term encompass all organisms with cells that exhibit the usual characteristics of eukaryotes, such as the presence of a true nucleus bounded by a nuclear membrane, within which lie the chromosomes, the presence of membrane-bound organelles, and other characteristics commonly observed in eukaryotic organisms. Thus, the term includes, but is not limited to such organisms as fungi, protozoa, and animals (e.g., humans).

As used herein, the term "in vitro" refers to an artificial environment and to processes or reactions that occur within an artificial environment. In vitro environments can consist of, but are not limited to, test tubes and cell culture. The term "in vivo" refers to the natural environment (e.g., an animal or a cell) and to processes or reaction that occur within a natural environment.

The terms "test compound" and "candidate compound" refer to any chemical entity, pharmaceutical, drug, and the like that is a candidate for use to treat or prevent a disease, illness, sickness, or disorder of bodily function (e.g., cancer). Test compounds comprise both known and potential therapeutic compounds. A test compound can be determined to be therapeutic by screening using the screening methods of the present invention.

As used herein, the term "sample" is used in its broadest sense. In one sense, it is meant to include a specimen or culture obtained from any source, as well as biological and environmental samples. Biological samples may be obtained from animals (including humans) and encompass fluids, solids, tissues, and gases. Biological samples include blood products, such as plasma, serum and the like. Environmental samples include environmental material such as surface matter, soil, water, crystals and industrial samples. Such examples are not however to be construed as limiting the sample types applicable to the present invention.

DETAILED DESCRIPTION OF THE INVENTION p53-mediated tumor suppression is mainly determined by its apoptotic activity. Abrogation of p53-mediated apoptosis is a fundamental defect in human tumors. This makes functional restoration of the p53 death pathway a premier therapeutic target for a 'universal' cancer strategy, with the potential for enormous clinical payoffs. Experiments conducted during the course of development of the present invention demonstrated that exploiting the shortest known circuitry of p53 death signaling, e.g., the direct transcription-independent mitochondrial p53 death program, has therapeutic utility.

Up to the present invention, efforts focused on restoring transcription-mediated p53 apoptosis. One avenue of research has tried to identify small molecules that structurally rescue tumor-derived p53 mutant proteins. Two prototype compounds, CP-31398 and PRIMA-1, can restore transcriptional p53 function in cell-based assays in vitro and slow tumor growth in tumor xenografts in nude mice. However, their mechanism of action is unclear (Foster et al., 1999. Science 286:2507-2510; Bykov et al., 2002. Nat Med 8:282-288) and their in vivo efficacy in natural mouse models of cancer as well as in cancer patients is untested.

Another area of research has focused on supplying conventional wild type p53 via gene therapy (Moll, 2000. New p53-based strategies for cancer therapy. Eaton Publishing, Natick, Mass. 439-455 pp.). Several clinical phase I and II studies using intratumoral injections of adenoviral or retroviral vectors carrying conventional nuclear wild type p53 conducted in the USA and Europe initially did demonstrate that these reagents are well-tolerated and exhibit limited antitumoral activity (Moll, supra; Zeimet et al., 2003. Lancet Oncol. 4:415-422; Nemunaitis et al., 2000. J. Clin. Oncol. 18:609-622; Kuball et al., 2002. J Clin Oncol. 20:957-965; Vecil and Lang, 2003. J Neuro. Oncol. 65:237-246). However, the recent failure of the largest wild type p53 gene therapy trial strongly suggests that despite its rational approach, tumor cells thwart treatment modalities aimed at restoring the transcriptional p53 death function (Zeimet et al., supra). In this international randomized phase II/III clinical trial, adenoviral AdSCMV-wtp53 was given intraperitoneally in combination with standard chemotherapy to ovarian cancer patients harboring p53 mutations. However, the study was closed after the first interim analysis because no therapeutic benefit could be shown (Zeimet et al., supra). Two reasons might account for this failure. Both the wtp53 and small molecule approach have in common that they rely on the preserved ability of tumor cells to respond with transcriptional activation of p53 target genes. However, many human cancers have lost this prerequisite due to global epigenetic dysregulation of their genome leading to broadly aberrant gene silencing patterns (Herman and Baylin, 2003. N Eng. J Med 349:2042-2054). In addition, wtp53 as a transcription factor works as a homo-tetramer mediated via its C-terminal tetramerization domain. This fact makes ectopic wtp53 protein vulnerable to so-called dominant negative inhibition by endogenous p53 mutants that are naturally expressed at very high levels in cancer tissues. About 50% of human cancers express mutant rather than wild type p53 proteins. An additional vulnerability for dominant negative interference of ectopic wtp53 protein emanates from deltaN isoforms of p63 and p73, which are also frequently overexpressed in human cancers (Concin et al., Moll. 2004. Cancer Res 64:2449-2460; Moll UM, Slade N. 2004. Mol Cancer Res 2: 371-386; Moll et al., 2001. Biochim Biophys Acta 1552:47-59).

p53-dependent apoptosis mainly utilizes the intrinsic mitochondrial pathway (Schuler and Green. 2001. Biochem Soc Trans 29:684-688). Apoptosis relies upon a pre-assembled death machinery of protein and DNA degrading enzymes that do not require transcription of new genes. Indeed, apoptosis can be triggered and proceed to its biochemical endpoint in nuclei-free cytoplast (Jacobson et al., Embo J 13:1899-1910; Martin et al., 1996. J Biol Chem 271:28753-28756; Schulze-Osthoff et al., 1994. J Cell Biol. 127: 15-20).

Experiments conducted during the course of development of the present invention demonstrated a fraction of the stress-induced endogenous p53 in normal and tumor cells naturally travels to mitochondria where it directly triggers permeabilization of the outer mitochondrial membrane with release of a host of factors that activate apoptosis of the cell (Marchenko et al., Moll. 2000. J Biol. Chem. 275:16202-16212; Sansome et al., Moll. 2001. FEBS Lett. 488: 110-115. Mihara et al., Moll. 2003. Molecular Cell, 11: 577-790. This biological fact is exploited in the present invention, which demonstrates that transcriptional p53 restoration (taking place in the cell nucleus) is dispensable for tumor killing in vivo. Instead, tumor cell regression is achieved by exploiting the direct and rapid transcription-independent apoptotic p53 program triggered from mitochondria. Mitochondrial p53 utilizes its DNA-binding domain, which is also central for its transcriptional role to inhibit the anti-apoptotic Bclx1/Bcl2 proteins located on the outer mitochondrial membrane and to induce BAK oligomerization that enables subsequent cytochrome C release (Mihara et al., 2003. Methods Mol Biol 234:203). Nuclear magnetic resonance studies confirmed that the BclXI interaction surface on p53 involves the same region that is used to contact DNA (Petros et al., 2004. FEBS Letters 28073:1-4). However, in contrast to transcriptionally active p53, mitochondrial p53 does not require tetramerization since its C-terminal domain is fully dispensable. The present invention is not limited to a particular mechanism. Indeed, an understanding of the mechanism is not necessary to practice the present invention. Nonetheless, it is contemplated that this provides another advantage in that mitochondrially targeted p53 might escape dominant negative inhibition by endogenous mutant p53 proteins and by delta Np63/p73 isoforms overexpressed in tumors. Together, its transcription-independence and potential escape from dominant negative interference provides a therapeutic modality.

Experiments conducted during the course of development of the present invention demonstrated that p53CTB strictly targets to mitochondria. p53CTM primarily targets to mitochondria, with some additional targeting to the endoplasmic reticulum. No detectable targeting to the nucleus or other organelles was observed. No detectable targeting to the nucleus or other organelles was observed. Mitochondrially targeted p53 lacks transcriptional activity and does not rely on transactivation, transrepression and is independent of epigenetic silencing, which is very common in human cancers and could pose a serious roadblock for any reagent that requires DNA binding and transcriptional action. Further experiments conducted during the course of development of the present invention demonstrated that mitochondrially targeted p53 promotes apoptosis in primary lymphoma cells in vitro. Further experiments demonstrated that mitochondrially targeted p53 kills primary lymphoma cells in vivo in well characterized mouse model for human Burkitt's lymphoma (This model is driven by the c-Myc oncogene and carries inactivating mutations in the ARF/p53 tumor suppressor axis).

Accordingly, in some embodiments, the present invention provides methods of inducing apoptosis (e.g., in cancer cells) and thus treating diseases such as cancer and autoimmune diseases that are characterized by defects in apoptotic pathways. The present invention further provides methods of screening for compounds that alter (e.g., rescue) mutant mitochondrial p53.

I. Apoptotic Inducing Therapies

In some embodiments, the present invention provides therapies for cancer. In some preferred embodiments, therapies target p53 to the mitochondria. However, the present invention is not limited to the treatment of cancer. The methods and compositions of the present invention are suitable for use in the treatment of any condition characterized by defects in apoptotic pathways including, but not limited to, cancer and autoimmune diseases. In some embodiments, the therapies are genetic therapies. In other embodiments, the therapies are small molecule therapies.

A. Genetic Therapies

In some embodiments, the present invention provides genetic treatments for altering apoptotic pathways. The present invention contemplates the use of any genetic manipulation for use in targeting the expression of p53 to the mitochondria (e.g., of cancer cells). In preferred embodiments, the p53 is delivered as a fusion protein fused to a mitochondrial targeting sequence. The present invention is not limited to a particular mitochondrial targeting sequence. Indeed, a variety of mitochondrial targeting sequences are contemplated including, but not limited to, BclX1 protein and Bcl2 protein. In some preferred embodiments, BclXI is the targeting sequence. In particularly preferred embodiments, the p53CTB vector described by SEQ ID NOs: 1 and 2 is utilized.

Delivery of nucleic acid constructs to cells in vitro or in vivo may be conducted using any suitable method. A suitable method is one that introduces the nucleic acid construct into the cell such that the desired event occurs (e.g., expression of p53 protein in mitochondria).

Introduction of molecules carrying genetic information into cells is achieved by any of various methods including, but not limited to, directed injection of naked DNA constructs, bombardment with gold particles loaded with said constructs, and macromolecule mediated gene transfer using, for example, liposomes, biopolymers, and the like. Preferred methods use gene delivery vehicles derived from viruses, including, but not limited to, adenoviruses, retroviruses, vaccinia viruses, and adeno-associated viruses. Exemplary methods are described in greater detail below.

1. Adenoviral Vectors

In some embodiments, adenoviral vectors are utilized for delivery of p53 to mitochondria. Self-propagating adenovirus (Ad) vectors have been extensively utilized to deliver foreign genes to a great variety of cell types in vitro and in vivo. "Self-propagating viruses" are those which can be produced by transfection of a single piece of DNA (the recombinant viral genome) into a single packaging cell line to produce infectious virus; self-propagating viruses do not require the use of helper virus for propagation. As with many vectors, adenoviral vectors have limitations on the amount of heterologous nucleic acid they are capable of delivering to cells. For example, the capacity of adenovirus is approximately 8-10 kb, the capacity of adeno-associated virus is approximately 4.8 kb, and the capacity of *lentivirus* is approximately 8.9 kb.

In an effort to address the viral replication problems associated with first generation Ad vectors, so called "second generation" Ad vectors have been developed. Second generation Ad vectors delete the early regions of the Ad genome (E2A, E2B, and E4). Highly modified second generation Ad vectors are less likely to generate replication-competent virus during large-scale vector preparation, and complete inhabitation of Ad genome replication should abolish late gene replication. Host immune response against late viral proteins is thus reduced [See Amalfitano et al., J. Virol. 72:926-933 (1998)]. The elimination of E2A, E2B, and E4 genes from the Ad genome also provide increased cloning capacity. The deletion of two or more of these genes from the Ad genome allows for example, the delivery of full length or cDNA genes via Ad vectors [Kumar-Singh et al, *Hum. Mol. Genet.*, 5:913 (1996)].

"Gutted," or helper dependent, Ad vectors contain cis-acting DNA sequences that direct adenoviral replication and packaging but do not contain viral coding sequences [See Fisher et al. *Virology* 217:11-22 (1996) and Kochanek et al. *Proc. Nat. Acad. Sci. USA* 93:5731-5736 (1996)]. Gutted vectors are defective viruses produced by replication in the presence of a helper virus, which provides all of the necessary viral proteins in trans. Since gutted vectors do not contain any viral genes, expression of viral proteins is not possible.

Recent developments have advanced the field of gutted vector production [See Hardy et al., J. Virol. 71:1842-1849 (1997) and Hartigan-O'Conner et al., *J. Virol.* 73:7835-7841 (1999)]. Gutted Ad vectors are able to maximally accommodate up to about 37 kb of exogenous DNA, however, 28-30 kb is more typical. For example, a gutted Ad vector can accommodate a full length gene or cDNA, but also expression cassettes or modulator proteins.

2. Lentiviral Vectors

Vectors based on human or feline *lentiviruses* have emerged as another vector useful for gene therapy applications. *Lentivirus*-based vectors infect nondividing cells as part of their normal life cycles, and are produced by expression of a package-able vector construct in a cell line that expresses viral proteins. The small size of lentiviral particles constrains the amount of exogenous DNA they are able to carry to about 10 kb.

3. Retroviral Vectors

Retroviruses (family Retroviridae) are divided into three groups: the *spumaviruses* (e.g., human foamy virus); the *lentiviruses* (e.g., human immunodeficiency virus and sheep visna virus) and the *oncoviruses* (e.g., MLV, Rous sarcoma virus).

Retroviruses are enveloped (i.e., surrounded by a host cell-derived lipid bilayer membrane) single-stranded RNA viruses that infect animal cells. When a retrovirus infects a cell, its RNA genome is converted into a double-stranded linear DNA form (i.e., it is reverse transcribed). The DNA form of the virus is then integrated into the host cell genome as a provirus. The provirus serves as a template for the production of additional viral genomes and viral mRNAs. Mature viral particles containing two copies of genomic RNA bud from the surface of the infected cell. The viral particle comprises the genomic RNA, reverse transcriptase and otherpol gene products inside the viral capsid (which contains the viral gag gene products), which is surrounded by a lipid bilayer membrane derived from the host cell containing the viral envelope glycoproteins (also referred to as membrane-associated proteins).

The organization of the genomes of numerous retroviruses is well known in the art and this has allowed the adaptation of the retroviral genome to produce retroviral vectors. The production of a recombinant retroviral vector carrying a gene of interest is typically achieved in two stages. First, the gene of interest is inserted into a retroviral vector which contains the sequences necessary for the efficient expression of the gene of interest (including promoter and/or enhancer elements which may be provided by the viral long terminal repeats [LTRs] or by an internal promoter/enhancer and relevant splicing signals), sequences required for the efficient packaging of the viral RNA into infectious virions (e.g., the packaging signal [Psi], the tRNA primer binding site [−PBS], the 3' regulatory sequences required for reverse transcription [+PBS] and the viral LTRs). The LTRs contain sequences required for the association of viral genomic RNA, reverse transcriptase and integrase functions, and sequences involved in directing the expression of the genomic RNA to be packaged in viral particles. For safety reasons, many recombinant retroviral vectors lack functional copies of the genes that are essential for viral replication (these essential genes are either deleted or disabled); the resulting virus is said to be replication defective.

Second, following the construction of the recombinant vector, the vector DNA is introduced into a packaging cell line. Packaging cell lines provide viral proteins required in trans for the packaging of the viral genomic RNA into viral particles having the desired host range (i.e., the viral-encoded gag, pol and env proteins). The host range is controlled, in part, by the type of envelope gene product expressed on the surface of the viral particle. Packaging cell lines may express ecotrophic, amphotropic or xenotropic envelope gene products. Alternatively, the packaging cell line may lack sequences encoding a viral envelope (env) protein. In this case the packaging cell line will package the viral genome into particles that lack a membrane-associated protein (e.g., an env protein). In order to produce viral particles containing a membrane associated protein that will permit entry of the virus into a cell, the packaging cell line containing the retroviral sequences is transfected with sequences encoding a membrane-associated protein (e.g., the G protein of vesicular stomatitis virus [VSV]). The transfected packaging cell will then produce viral particles that contain the membrane-associated protein expressed by the transfected packaging cell line; these viral particles, which contain viral genomic RNA derived from one virus encapsidated by the envelope proteins of another virus are said to be pseudotyped virus particles.

The most commonly used recombinant retroviral vectors are derived from the amphotropic Moloney murine leukemia virus (MoMLV) (Miller and Baltimore, Mol. Cell. Biol., 6:2895 [1986]). The MoMLV system has several advantages: 1) this specific retrovirus can infect many different cell types, 2) established packaging cell lines are available for the production of recombinant MoMLV viral particles and 3) the transferred genes are permanently integrated into the target cell chromosome. The established MoMLV vector systems comprise a DNA vector containing a small portion of the retroviral sequence (the viral long terminal repeat or "LTR" and the packaging or "psi" signal) and a packaging cell line. The gene to be transferred is inserted into the DNA vector. The viral sequences present on the DNA vector provide the signals necessary for the insertion or packaging of the vector RNA into the viral particle and for the expression of the inserted gene. The packaging cell line provides the viral proteins required for particle assembly (Markowitz et al., J. Virol., 62:1120 [1988]).

Despite these advantages, existing retroviral vectors based upon MoMLV are limited by several intrinsic problems: 1) they do not infect non-dividing cells (Miller et al., Mol. Cell. Biol., 10:4239 [1992]), 2) they produce low titers of the recombinant virus (Miller and Rosman, BioTechn., 7: 980 [1989]; and Miller, Nature 357: 455 [1992]) and 3) they infect certain cell types (e.g., human lymphocytes) with low efficiency (Adams et al., Proc. Natl. Acad. Sci. USA 89:8981 [1992]). The low titers associated with MoMLV-based vectors has been attributed, at least in part, to the instability of the virus-encoded envelope protein. Concentration of retrovirus stocks by physical means (e.g., ultracentrifugation and ultrafiltration) leads to a severe loss of infectious virus.

The low titer and inefficient infection of certain cell types by MoMLV-based vectors has been overcome by the use of pseudotyped retroviral vectors that contain the G protein of VSV as the membrane associated protein. Unlike retroviral envelope proteins which bind to a specific cell surface protein receptor to gain entry into a cell, the VSV G protein interacts with a phospholipid component of the plasma membrane (Mastromarino et al., J. Gen. Virol., 68:2359 [1977]). Because entry of VSV into a cell is not dependent upon the presence of specific protein receptors, VSV has an extremely broad host range. Pseudotyped retroviral vectors bearing the VSV G protein have an altered host range characteristic of VSV (i.e., they can infect almost all species of vertebrate, invertebrate and insect cells). Importantly, VSV G-pseudotyped retroviral vectors can be concentrated 2000-fold or more by ultracentrifugation without significant loss of infectivity (Burns et al., Proc. Natl. Acad. Sci. USA, 90:8033 [1993]).

The VSV G protein has also been used to pseudotype retroviral vectors based upon the human immunodeficiency virus (HIV) (Naldini et al., Science 272:263 [1996]). Thus, the VSV G protein may be used to generate a variety of pseudotyped retroviral vectors and is not limited to vectors based on MoMLV.

4. Delivery of Vectors

Vectors may be administered to subjects in a variety of ways. For example, in some embodiments of the present invention, vectors are administered into tumors or tissue associated with tumors using direct injection. In other embodiments, administration is via the blood or lymphatic circulation (See e.g., PCT publication 99/02685 herein incorporated by reference in its entirety). Exemplary dose levels of adenoviral vector are preferably $10^8$ to $10^{11}$ vector particles added to the perfusate.

B. Combination Therapy

The present invention is not limited to the expression of mitochondrial p53. In certain embodiments, the present invention contemplates combination therapies. For example, in some embodiments, both nuclear p53 and mitochondrial p53 are utilized in cancer therapy (e.g., genetic therapies). Such combination therapies find use in killing cancer cells that carry p53 missense mutations. The present invention is not limited to a particular mechanism. Indeed, an understanding of the mechanism is not necessary to practice the present invention. Nonetheless, it is contemplated that the combination of mitochondrial and nuclear p53 provides a synergistic effect in inducing apoptosis in cancer cells.

In other embodiments, the compositions of the present invention are provided in combination with existing therapies. In some embodiments, the compounds of the present invention are provided in combination with known cancer chemotherapy agents. The present invention is not limited to a particular chemotherapy agent.

Various classes of antineoplastic (e.g., anticancer) agents are contemplated for use in certain embodiments of the present invention. Anticancer agents suitable for use with the present invention include, but are not limited to, agents that induce apoptosis, agents that inhibit adenosine deaminase function, inhibit pyrimidine biosynthesis, inhibit purine ring biosynthesis, inhibit nucleotide interconversions, inhibit ribonucleotide reductase, inhibit thymidine monophosphate (TMP) synthesis, inhibit dihydrofolate reduction, inhibit DNA synthesis, form adducts with DNA, damage DNA, inhibit DNA repair, intercalate with DNA, deaminate asparagines, inhibit RNA synthesis, inhibit protein synthesis or stability, inhibit microtubule synthesis or function, and the like.

In some embodiments, exemplary anticancer agents suitable for use in compositions and methods of the present invention include, but are not limited to: 1) alkaloids, including microtubule inhibitors (e.g., vincristine, vinblastine, and vindesine, etc.), microtubule stabilizers (e.g., paclitaxel (TAXOL), and docetaxel, etc.), and chromatin function inhibitors, including topoisomerase inhibitors, such as epipodophyllotoxins (e.g., etoposide (VP-16), and teniposide (VM-26), etc.), and agents that target topoisomerase I (e.g., camptothecin and isirinotecan (CPT-11), etc.); 2) covalent DNA-binding agents (alkylating agents), including nitrogen mustards (e.g., metchlorethamine, chlorambucil, cyclophosphamide, ifosphamide, and busulfan (MYLERAN), etc.), nitrosoureas (e.g., carmustine, lomustine, and semustine, etc.), and other alkylating agents (e.g., dacarbazine, hydroxymethylmelamine, thiotepa, and mitomycin, etc.); 3) noncovalent DNA-binding agents (antitumor antibiotics), including nucleic acid inhibitors (e.g., dactinomycin (actinomycin D), etc.), anthracyclines (e.g., daunorubicin (daunomycin, and cerubidine), doxorubicin (adriamycin), and idarubicin (idamycin), etc.), anthracenediones (e.g., anthracycline analogues, such as mitoxantrone, etc.), bleomycins (BLENOXANE), etc., and plicamycin (mithramycin), etc.; 4) antimetabolites, including antifolates (e.g., methotrexate, FOLEX, and MEXATE, etc.), purine antimetabolites (e.g., 6-mercaptopurine (6-MP, PURINETHOL), 6-thioguanine (6-TG), azathioprine, acyclovir, ganciclovir, chlorodeoxyadenosine, 2-chlorodeoxyadenosine (CdA), and 2'-deoxycoformycin (pentostatin), etc.), pyrimidine antagonists (e.g., fluoropyrimidines (e.g., 5-fluorouracil (ADRUCIL), 5-fluorodeoxyuridine (FdUrd) (floxuridine)) etc.), and cytosine arabinosides (e.g., CYTOSAR (ara-C) and fludarabine, etc.); 5) enzymes, including L-asparaginase, and hydroxyurea, etc.; 6) hormones, including glucocorticoids, antiestrogens (e.g., tamoxifen, etc.), nonsteroidal antiandrogens (e.g., flutamide, etc.), and aromatase inhibitors (e.g., anastrozole (ARIMIDEX), etc.); 7) platinum compounds (e.g., cisplatin and carboplatin, etc.); 8) monoclonal antibodies conjugated with anticancer drugs, toxins, and/or radionuclides, etc.; 9) biological response modifiers (e.g., interferons (e.g., IFN-α, etc.) and interleukins (e.g., IL-2, etc.), etc.); 10) adoptive immunotherapy; 11) hematopoietic growth factors; 12) agents that induce tumor cell differentiation (e.g., all-trans-retinoic acid, etc.); 13) gene therapy techniques; 14) antisense therapy techniques; 15) tumor vaccines; 16) therapies directed against tumor metastases (e.g., batimastat, etc.); 17) angiogenesis inhibitors; 18) proteosome inhibitors (e.g., VELCADE); 19) inhibitors of acetylation and/or methylation (e.g., HDAC inhibitors); 20) modulators of NF kappa B; 21) inhibitors of cell cycle regulation (e.g., CDK inhibitors); 22) modulators of p53 protein function; and 23) ionizing radiation.

Any oncolytic agent that is routinely used in a cancer therapy context finds use in the compositions and methods of the present invention. For example, the U.S. Food and Drug Administration maintains a formulary of oncolytic agents approved for use in the United States. International counterpart agencies to the U.S.F.D.A. maintain similar formularies. Table 4 provides a list of exemplary antineoplastic agents approved for use in the U.S. Those skilled in the art will appreciate that the "product labels" required on all U.S. approved chemotherapeutics describe approved indications, dosing information, toxicity data, and the like, for the exemplary agents.

TABLE 4

| | | |
|---|---|---|
| Aldesleukin (des-alanyl-1, serine-125 human interleukin-2) | Proleukin | Chiron Corp., Emeryville, CA |
| Alemtuzumab (IgG1κ anti CD52 antibody) | Campath | Millennium and ILEX Partners, LP, Cambridge, MA |
| Alitretinoin (9-cis-retinoic acid) | Panretin | Ligand Pharmaceuticals, Inc., San Diego CA |
| Allopurinol (1,5-dihydro-4H-pyrazolo[3,4-d]pyrimidin-4-one monosodium salt) | Zyloprim | GlaxoSmithKline, Research Triangle Park, NC |
| Altretamine (N,N,N',N',N'',N''-hexamethyl-1,3,5-triazine-2,4,6-triamine) | Hexalen | US Bioscience, West Conshohocken, PA |
| Amifostine (ethanethiol, 2-[(3-aminopropyl)amino]-, dihydrogen phosphate (ester)) | Ethyol | US Bioscience |
| Anastrozole (1,3-Benzenediacetonitrile, a,a,a',a'-tetramethyl-5-(1H-1,2,4-triazol-1-ylmethyl)) | Arimidex | AstraZeneca Pharmaceuticals, LP, Wilmington, DE |
| Arsenic trioxide | Trisenox | Cell Therapeutic, Inc., Seattle, WA |
| Asparaginase (L-asparagine amidohydrolase, type EC-2) | Elspar | Merck & Co., Inc., Whitehouse Station, NJ |
| BCG Live (lyophilized preparation of an attenuated strain of *Mycobacterium bovis* (*Bacillus Calmette-Gukin* [BCG], substrain Montreal) | TICE BCG | Organon Teknika, Corp., Durham, NC |
| bexarotene capsules (4-[1-(5,6,7,8-tetrahydro-3,5,5,8,8-pentamethyl-2-napthalenyl) ethenyl] benzoic acid) | Targretin | Ligand Pharmaceuticals |
| bexarotene gel | Targretin | Ligand Pharmaceuticals |
| Bleomycin (cytotoxic glycopeptide antibiotics produced by *Streptomyces verticillus*; bleomycin $A_2$ and bleomycin $B_2$) | Blenoxane | Bristol-Myers Squibb Co., NY, NY |
| Capecitabine (5'-deoxy-5-fluoro-N-[(pentyloxy)carbonyl]-cytidine) | Xeloda | Roche |
| Carboplatin (platinum, diammine [1,1-cyclobutanedicarboxylato(2-)-0,0']-,(SP-4-2)) | Paraplatin | Bristol-Myers Squibb |
| Carmustine (1,3-bis(2-chloroethyl)-1-nitrosourea) | BCNU, BiCNU | Bristol-Myers Squibb |
| Carmustine with Polifeprosan 20 Implant | Gliadel Wafer | Guilford Pharmaceuticals, Inc., Baltimore, MD |
| Celecoxib (as 4-[5-(4-methylphenyl)-3-(trifluoromethyl)-1H-pyrazol-1-yl] benzenesulfonamide) | Celebrex | Searle Pharmaceuticals, England |
| Chlorambucil (4-[bis(2chlorethyl)amino]benzenebutanoic acid) | Leukeran | GlaxoSmithKline |
| Cisplatin ($PtCl_2H_6N_2$) | Platinol | Bristol-Myers Squibb |
| Cladribine (2-chloro-2'-deoxy-b-D-adenosine) | Leustatin, 2-CdA | R. W. Johnson Pharmaceutical Research Institute, Raritan, NJ |
| Cyclophosphamide (2-[bis(2-chloroethyl)amino] tetrahydro-2H-13,2-oxazaphosphorine 2-oxide monohydrate) | Cytoxan, Neosar | Bristol-Myers Squibb |

TABLE 4-continued

| | | |
|---|---|---|
| Cytarabine (1-b-D-Arabinofuranosylcytosine, $C_9H_{13}N_3O_5$) | Cytosar-U | Pharmacia & Upjohn Company |
| cytarabine liposomal | DepoCyt | Skye Pharmaceuticals, Inc., San Diego, CA |
| Dacarbazine (5-(3,3-dimethyl-1-triazeno)-imidazole-4-carboxamide (DTIC)) | DTIC-Dome | Bayer AG, Leverkusen, Germany |
| Dactinomycin, actinomycin D (actinomycin produced by *Streptomyces parvullus*, $C_{62}H_{86}N_{12}O_{16}$) | Cosmegen | Merck |
| Darbepoetin alfa (recombinant peptide) | Aranesp | Amgen, Inc., Thousand Oaks, CA |
| daunorubicin liposomal ((8S-cis)-8-acetyl-10-[(3-amino-2,3,6-trideoxy-a-L-lyxo-hexopyranosyl)oxy]-7,8,9,10-tetrahydro-6,8,11-trihydroxy-1-methoxy-5,12-naphthacenedione hydrochloride) | DanuoXome | Nexstar Pharmaceuticals, Inc., Boulder, CO |
| Daunorubicin HCl, daunomycin ((1S,3S)-3-Acetyl-1,2,3,4,6,11-hexahydro-3,5,12-trihydroxy-10-methoxy-6,11-dioxo-1-naphthacenyl 3-amino-2,3,6-trideoxy-(alpha)-L-lyxo-hexopyranoside hydrochloride) | Cerubidine | Wyeth Ayerst, Madison, NJ |
| Denileukin diftitox (recombinant peptide) | Ontak | Seragen, Inc., Hopkinton, MA |
| Dexrazoxane ((S)-4,4'-(1-methyl-1,2-ethanediyl)bis-2,6-piperazinedione) | Zinecard | Pharmacia & Upjohn Company |
| Docetaxel ((2R,3S)-N-carboxy-3-phenylisoserine, N-tert-butyl ester, 13-ester with 5b-20-epoxy-12a,4,7b,10b,13a-hexahydroxytax-11-en-9-one 4-acetate 2-benzoate, trihydrate) | Taxotere | Aventis Pharmaceuticals, Inc., Bridgewater, NJ |
| Doxorubicin HCl (8S,10S)-10-[(3-amino-2,3,6-trideoxy-a-L-lyxo-hexopyranosyl)oxy]-8-glycolyl-7,8,9,10-tetrahydro-6,8,11-trihydroxy-1-methoxy-5,12-naphthacenedione hydrochloride) | Adriamycin, Rubex | Pharmacia & Upjohn Company |
| doxorubicin | Adriamycin PFS Intravenous injection | Pharmacia & Upjohn Company |
| doxorubicin liposomal | Doxil | Sequus Pharmaceuticals, Inc., Menlo park, CA |
| dromostanolone propionate (17b-Hydroxy-2a-methyl-5a-androstan-3-one propionate) | Dromostanolone | Eli Lilly & Company, Indianapolis, IN |
| dromostanolone propionate | Masterone injection | Syntex, Corp., Palo Alto, CA |
| Elliott's B Solution | Elliott's B Solution | Orphan Medical, Inc |
| Epirubicin ((8S-cis)-10-[(3-amino-2,3,6-trideoxy-a-L-arabino-hexopyranosyl)oxy]-7,8,9,10-tetrahydro-6,8,11-trihydroxy-8-(hydroxyacetyl)-1-methoxy-5,12-naphthacenedione hydrochloride) | Ellence | Pharmacia & Upjohn Company |
| Epoetin alfa (recombinant peptide) | Epogen | Amgen, Inc |
| Estramustine (estra-1,3,5(10)-triene-3,17-diol(17(beta))-, 3-[bis(2-chloroethyl)carbamate] 17-(dihydrogen phosphate), disodium salt, monohydrate, or estradiol 3-[bis(2-chloroethyl)carbamate] 17-(dihydrogen phosphate), disodium salt, monohydrate) | Emcyt | Pharmacia & Upjohn Company |
| Etoposide phosphate (4'-Demethylepipodophyllotoxin 9-[4,6-O-(R)-ethylidene-(beta)-D-glucopyranoside], 4'-(dihydrogen phosphate)) | Etopophos | Bristol-Myers Squibb |
| etoposide, VP-16 (4'-demethylepipodophyllotoxin 9-[4,6-0-(R)-ethylidene-(beta)-D-glucopyranoside]) | Vepesid | Bristol-Myers Squibb |
| Exemestane (6-methylenandrosta-1,4-diene-3,17-dione) | Aromasin | Pharmacia & Upjohn Company |
| Filgrastim (r-metHuG-CSF) | Neupogen | Amgen, Inc |
| floxuridine (intraarterial) (2'-deoxy-5-fluorouridine) | FUDR | Roche |
| Fludarabine | Fludara | Berlex Laboratories, |

TABLE 4-continued

| | | |
|---|---|---|
| (fluorinated nucleotide analog of the antiviral agent vidarabine, 9-b-D-arabinofuranosyladenine (ara-A)) | | Inc., Cedar Knolls, NJ |
| Fluorouracil, 5-FU (5-fluoro-2,4(1H,3H)-pyrimidinedione) | Adrucil | ICN Pharmaceuticals, Inc., Humacao, Puerto Rico |
| Fulvestrant (7-alpha-[9-(4,4,5,5,5-penta fluoropentylsulphinyl) nonyl]estra-1,3,5-(10)-triene-3,17-beta-diol) | Faslodex | IPR Pharmaceuticals, Guayama, Puerto Rico |
| Gemcitabine (2'-deoxy-2',2'-difluorocytidine monohydrochloride (b-isomer)) | Gemzar | Eli Lilly |
| Gemtuzumab Ozogamicin (anti-CD33 hP67.6) | Mylotarg | Wyeth Ayerst |
| Goserelin acetate (acetate salt of [D-Ser(But)$^6$,Azgly$^{10}$]LHRH; pyro-Glu-His-Trp-Ser-Tyr-D-Ser(But)-Leu-Arg-Pro-Azgly-NH2 acetate [$C_{59}H_{84}N_{18}O_{14}$·($C_2H_4O_2$)$_x$ | Zoladex Implant | AstraZeneca Pharmaceuticals |
| Hydroxyurea | Hydrea | Bristol-Myers Squibb |
| Ibritumomab Tiuxetan (immunoconjugate resulting from a thiourea covalent bond between the monoclonal antibody Ibritumomab and the linker-chelator tiuxetan [N-[2-bis(carboxymethyl)amino]-3-(p-isothiocyanatophenyl)-propyl]-[N-[2-bis(carboxymethyl)amino]-2-(methyl)-ethyl]glycine) | Zevalin | Biogen IDEC, Inc., Cambridge MA |
| Idarubicin (5,12-Naphthacenedione, 9-acetyl-7-[(3-amino-2,3,6-trideoxy-(alpha)-L-lyxo-hexopyranosyl)oxy]-7,8,9,10-tetrahydro-6,9,11-trihydroxyhydrochloride, (7S-cis)) | Idamycin | Pharmacia & Upjohn Company |
| Ifosfamide (3-(2-chloroethyl)-2-[(2-chloroethyl)amino]tetrahydro-2H-1,3,2-oxazaphosphorine 2-oxide) | IFEX | Bristol-Myers Squibb |
| Imatinib Mesilate (4-[(4-Methyl-1-piperazinyl)methyl]-N-[4-methyl-3-[[4-(3-pyridinyl)-2-pyrimidinyl]amino]-phenyl]benzamide methanesulfonate) | Gleevec | Novartis AG, Basel, Switzerland |
| Interferon alfa-2a (recombinant peptide) | Roferon-A | Hoffmann-La Roche, Inc., Nutley, NJ |
| Interferon alfa-2b (recombinant peptide) | Intron A (Lyophilized Betaseron) | Schering AG, Berlin, Germany |
| Irinotecan HCl ((4S)-4,11-diethyl-4-hydroxy-9-[(4-piperidinopiperidino) carbonyloxy]-1H-pyrano[3',4': 6,7] indolizino[1,2-b] quinoline-3,14(4H,12H) dione hydrochloride trihydrate) | Camptosar | Pharmacia & Upjohn Company |
| Letrozole (4,4'-(1H-1,2,4-Triazol-1-ylmethylene) dibenzonitrile) | Femara | Novartis |
| Leucovorin (L-Glutamic acid, N[4[[(2amino-5-formyl-1,4,5,6,7,8 hexahydro4oxo6-pteridinyl)methyl]amino]benzoyl], calcium salt (1:1)) | Wellcovorin, Leucovorin | Immunex, Corp., Seattle, WA |
| Levamisole HCl ((-)-(S)-2,3,5,6-tetrahydro-6-phenylimidazo [2,1-b] thiazole monohydrochloride $C_{11}H_{12}N_2S$·HCl) | Ergamisol | Janssen Research Foundation, Titusville, NJ |
| Lomustine (1-(2-chloro-ethyl)-3-cyclohexyl-1-nitrosourea) | CeeNU | Bristol-Myers Squibb |
| Mechlorethamine, nitrogen mustard (2-chloro-N-(2-chloroethyl)-N-methylethanamine hydrochloride) | Mustargen | Merck |
| Megestrol acetate 17α(acetyloxy)-6-methylpregna-4,6-diene-3,20-dione | Megace | Bristol-Myers Squibb |
| Melphalan, L-PAM (4-[bis(2-chloroethyl) amino]-L-phenylalanine) | Alkeran | GlaxoSmithKline |
| Mercaptopurine, 6-MP (1,7-dihydro-6H-purine-6-thione monohydrate) | Purinethol | GlaxoSmithKline |
| Mesna (sodium 2-mercaptoethane sulfonate) | Mesnex | Asta Medica |
| Methotrexate (N-[4-[[(2,4-diamino-6-pteridinyl)methyl]methylamino]benzoyl]-L-glutamic acid) | Methotrexate | Lederle Laboratories |

TABLE 4-continued

| | | |
|---|---|---|
| Methoxsalen (9-methoxy-7H-furo[3,2-g][1]-benzopyran-7-one) | Uvadex | Therakos, Inc., Way Exton, Pa |
| Mitomycin C | Mutamycin | Bristol-Myers Squibb |
| mitomycin C | Mitozytrex | SuperGen, Inc., Dublin, CA |
| Mitotane (1,1-dichloro-2-(o-chlorophenyl)-2-(p-chlorophenyl)ethane) | Lysodren | Bristol-Myers Squibb |
| Mitoxantrone (1,4-dihydroxy-5,8-bis[[2-[(2-hydroxyethyl)amino]ethyl]amino]-9,10-anthracenedione dihydrochloride) | Novantrone | Immunex Corporation |
| Nandrolone phenpropionate | Durabolin-50 | Organon, Inc., West Orange, NJ |
| Nofetumomab | Verluma | Boehringer Ingelheim Pharma KG, Germany |
| Oprelvekin (IL-11) | Neumega | Genetics Institute, Inc., Alexandria, VA |
| Oxaliplatin (cis-[(1R,2R)-1,2-cyclohexanediamine-N,N'] [oxalato(2-)-O,O'] platinum) | Eloxatin | Sanofi Synthelabo, Inc., NY, NY |
| Paclitaxel (5β,20-Epoxy-1,2a,4,7β,10β,13a-hexahydroxytax-11-en-9-one 4,10-diacetate 2-benzoate 13-ester with (2R,3S)-N-benzoyl-3-phenylisoserine) | TAXOL | Bristol-Myers Squibb |
| Pamidronate (phosphonic acid (3-amino-1-hydroxypropylidene) bis-, disodium salt, pentahydrate, (APD)) | Aredia | Novartis |
| Pegademase ((monomethoxypolyethylene glycol succinimidyl) 11-17-adenosine deaminase) | Adagen (Pegademase Bovine) | Enzon Pharmaceuticals, Inc., Bridgewater, NJ |
| Pegaspargase (monomethoxypolyethylene glycol succinimidyl L-asparaginase) | Oncaspar | Enzon |
| Pegfilgrastim (covalent conjugate of recombinant methionyl human G-CSF (Filgrastim) and monomethoxypolyethylene glycol) | Neulasta | Amgen, Inc |
| Pentostatin | Nipent | Parke-Davis Pharmaceutical Co., Rockville, MD |
| Pipobroman | Vercyte | Abbott Laboratories, Abbott Park, IL |
| Plicamycin, Mithramycin (antibiotic produced by *Streptomyces plicatus*) | Mithracin | Pfizer, Inc., NY, NY |
| Porfimer sodium | Photofrin | QLT Phototherapeutics, Inc., Vancouver, Canada |
| Procarbazine (N-isopropyl-μ-(2-methylhydrazino)-p-toluamide monohydrochloride) | Matulane | Sigma Tau Pharmaceuticals, Inc., Gaithersburg, MD |
| Quinacrine (6-chloro-9-(1-methyl-4-diethyl-amine) butylamino-2-methoxyacridine) | Atabrine | Abbott Labs |
| Rasburicase (recombinant peptide) | Elitek | Sanofi-Synthelabo, Inc., |
| Rituximab (recombinant anti-CD20 antibody) | Rituxan | Genentech, Inc., South San Francisco, CA |
| Sargramostim (recombinant peptide) | Prokine | Immunex Corp |
| Streptozocin (streptozocin 2-deoxy-2-[[(methylnitrosoamino)carbonyl]amino]-a(and b)-D-glucopyranose and 220 mg citric acid anhydrous) | Zanosar | Pharmacia & Upjohn Company |
| Talc ($Mg_3Si_4O_{10}(OH)_2$) | Sclerosol | Bryan, Corp., Woburn, MA |
| Tamoxifen ((Z)2-[4-(1,2-diphenyl-1-butenyl)phenoxy]-N,N-dimethylethanamine 2-hydroxy-1,2,3-propanetricarboxylate (1:1)) | Nolvadex | AstraZeneca Pharmaceuticals |
| Temozolomide (3,4-dihydro-3-methyl-4-oxoimidazo[5,1-d]-as-tetrazine-8-carboxamide) | Temodar | Schering |
| Teniposide, VM-26 | Vumon | Bristol-Myers Squibb |

TABLE 4-continued

| | | |
|---|---|---|
| (4'-demethylepipodophyllotoxin 9-[4,6-0-(R)-2-thenylidene-(beta)-D-glucopyranoside]) | | |
| Testolactone (13-hydroxy-3-oxo-13,17-secoandrosta-1,4-dien-17-oic acid [dgr]-lactone) | Teslac | Bristol-Myers Squibb |
| Thioguanine, 6-TG (2-amino-1,7-dihydro-6H-purine-6-thione) | Thioguanine | GlaxoSmithKline |
| Thiotepa (Aziridine,1,1',1''-phosphinothioylidynetris-,or Tris (1-aziridinyl) phosphine sulfide) | Thioplex | Immunex Corporation |
| Topotecan HCl ((S)-10-[(dimethylamino) methyl]-4-ethyl-4,9-dihydroxy-1H-pyrano[3',4':6,7] indolizino [1,2-b] quinoline-3,14-(4H,12H)-dione monohydrochloride) | Hycamtin | GlaxoSmithKline |
| Toremifene (2-(p-[(Z)-4-chloro-1,2-diphenyl-1-butenyl]-phenoxy)-N,N-dimethylethylamine citrate (1:1)) | Fareston | Roberts Pharmaceutical Corp., Eatontown, NJ |
| Tositumomab, I 131 Tositumomab (recombinant murine immunotherapeutic monoclonal IgG$_{2a}$ lambda anti-CD20 antibody(I 131 is a radioimmunotherapeutic antibody)) | Bexxar | Corixa Corp., Seattle, WA |
| Trastuzumab (recombinant monoclonal IgG$_1$ kappa anti-HER2 antibody) | Herceptin | Genentech, Inc |
| Tretinoin, ATRA (all-trans retinoic acid) | Vesanoid | Roche |
| Uracil Mustard | Uracil Mustard Capsules | Roberts Labs |
| Valrubicin, N-trifluoroacetyladriamycin-14-valerate ((2S-cis)-2-[1,2,3,4,6,11-hexahydro-2,5,12-trihydroxy-7 methoxy-6,11-dioxo-[[4 2,3,6-trideoxy-3-[(trifluoroacetyl)-amino-α-L-lyxo-hexopyranosyl]oxyl]-2-naphthacenyl]-2-oxoethyl pentanoate) | Valstar | Anthra --> Medeva |
| Vinblastine, Leurocristine (C$_{46}$H$_{56}$N$_4$O$_{10}$·H$_2$SO$_4$) | Velban | Eli Lilly |
| Vincristine (C$_{46}$H$_{56}$N$_4$O$_{10}$·H$_2$SO$_4$) | Oncovin | Eli Lilly |
| Vinorelbine (3',4'-didehydro-4'-deoxy-C'-norvincaleukoblastine [R-(R*,R*)-2,3-dihydroxybutanedioate (1:2)(salt)]) | Navelbine | GlaxoSmithKline |
| Zoledronate, Zoledronic acid ((1-Hydroxy-2-imidazol-1-yl-phosphonoethyl) phosphonic acid monohydrate) | Zometa | Novartis |

C. Small Molecule Drugs

In some embodiments, the present invention provides drugs (e.g., small molecule drugs) that reduce or eliminate cancer by reactivating (e.g., refolding) mutant mitochondrial p53. In some embodiments, small molecule drugs are identified using the drug screens described herein (e.g., in Section II below).

D. Pharmaceutical Compositions

The present invention further provides pharmaceutical compositions (e.g., comprising the therapeutic compounds described above). The pharmaceutical compositions of the present invention may be administered in a number of ways depending upon whether local or systemic treatment is desired and upon the area to be treated. Administration may be topical (including ophthalmic and to mucous membranes including vaginal and rectal delivery), pulmonary (e.g., by inhalation or insufflation of powders or aerosols, including by nebulizer; intratracheal, intranasal, epidermal and transdermal), oral or parenteral. Parenteral administration includes intravenous, intraarterial, subcutaneous, intraperitoneal or intramuscular injection or infusion; or intracranial, e.g., intrathecal or intraventricular, administration.

Pharmaceutical compositions and formulations for topical administration may include transdermal patches, ointments, lotions, creams, gels, drops, suppositories, sprays, liquids and powders. Conventional pharmaceutical carriers, aqueous, powder or oily bases, thickeners and the like may be necessary or desirable.

Compositions and formulations for oral administration include powders or granules, suspensions or solutions in water or non-aqueous media, capsules, sachets or tablets. Thickeners, flavoring agents, diluents, emulsifiers, dispersing aids or binders may be desirable.

Compositions and formulations for parenteral, intrathecal or intraventricular administration may include sterile aqueous solutions that may also contain buffers, diluents and other suitable additives such as, but not limited to, penetration enhancers, carrier compounds and other pharmaceutically acceptable carriers or excipients.

Pharmaceutical compositions of the present invention include, but are not limited to, solutions, emulsions, and liposome-containing formulations. These compositions may be generated from a variety of components that include, but are not limited to, preformed liquids, self-emulsifying solids and self-emulsifying semisolids.

The pharmaceutical formulations of the present invention, which may conveniently be presented in unit dosage form, may be prepared according to conventional techniques well known in the pharmaceutical industry. Such techniques include the step of bringing into association the active ingredients with the pharmaceutical carrier(s) or excipient(s). In general the formulations are prepared by uniformly and intimately bringing into association the active ingredients with liquid carriers or finely divided solid carriers or both, and then, if necessary, shaping the product.

The compositions of the present invention may be formulated into any of many possible dosage forms such as, but not limited to, tablets, capsules, liquid syrups, soft gels, suppositories, and enemas. The compositions of the present invention may also be formulated as suspensions in aqueous, non-aqueous or mixed media. Aqueous suspensions may further contain substances that increase the viscosity of the suspension including, for example, sodium carboxymethylcellulose, sorbitol and/or dextran. The suspension may also contain stabilizers.

In one embodiment of the present invention the pharmaceutical compositions may be formulated and used as foams. Pharmaceutical foams include formulations such as, but not limited to, emulsions, microemulsions, creams, jellies and liposomes. While basically similar in nature these formulations vary in the components and the consistency of the final product.

Agents that enhance uptake of oligonucleotides at the cellular level may also be added to the pharmaceutical and other compositions of the present invention. For example, cationic lipids, such as lipofectin (U.S. Pat. No. 5,705,188), cationic glycerol derivatives, and polycationic molecules, such as polylysine (WO 97/30731), also enhance the cellular uptake of oligonucleotides.

The compositions of the present invention may additionally contain other adjunct components conventionally found in pharmaceutical compositions. Thus, for example, the compositions may contain additional, compatible, pharmaceutically-active materials such as, for example, antipruritics, astringents, local anesthetics or anti-inflammatory agents, or may contain additional materials useful in physically formulating various dosage forms of the compositions of the present invention, such as dyes, flavoring agents, preservatives, antioxidants, opacifiers, thickening agents and stabilizers. However, such materials, when added, should not unduly interfere with the biological activities of the components of the compositions of the present invention. The formulations can be sterilized and, if desired, mixed with auxiliary agents, e.g., lubricants, preservatives, stabilizers, wetting agents, emulsifiers, salts for influencing osmotic pressure, buffers, colorings, flavorings and/or aromatic substances and the like which do not deleteriously interact with the pharmaceutical agents of the formulation.

Certain embodiments of the invention provide pharmaceutical compositions containing (a) one or more compounds of the present invention and (b) one or more other chemotherapeutic agents that function by a non-antisense mechanism. Examples of such chemotherapeutic agents include, but are not limited to, anticancer drugs such as daunorubicin, dactinomycin, doxorubicin, bleomycin, mitomycin, nitrogen mustard, chlorambucil, melphalan, cyclophosphamide, 6-mercaptopurine, 6-thioguanine, cytarabine (CA), 5-fluorouracil (5-FU), floxuridine (5-FUdR), methotrexate (MTX), colchicine, vincristine, vinblastine, etoposide, teniposide, cisplatin and diethylstilbestrol (DES). Anti-inflammatory drugs, including but not limited to nonsteroidal anti-inflammatory drugs and corticosteroids, and antiviral drugs, including but not limited to ribivirin, vidarabine, acyclovir and ganciclovir, may also be combined in compositions of the invention. Other non-antisense chemotherapeutic agents are also within the scope of this invention. Two or more combined compounds may be used together or sequentially.

Dosing is dependent on severity and responsiveness of the disease state to be treated, with the course of treatment lasting from several days to several months, or until a cure is effected or a diminution of the disease state is achieved. Optimal dosing schedules can be calculated from measurements of drug accumulation in the body of the patient. The administering physician can easily determine optimum dosages, dosing methodologies and repetition rates. Optimum dosages may vary depending on the relative potency of individual oligonucleotides, and can generally be estimated based on $EC_{50}$s found to be effective in in vitro and in vivo animal models or based on the examples described herein. In general, dosage is from 0.01 μg to 100 g per kg of body weight, and may be given once or more daily, weekly, monthly or yearly. The treating physician can estimate repetition rates for dosing based on measured residence times and concentrations of the drug in bodily fluids or tissues. Following successful treatment, it may be desirable to have the subject undergo maintenance therapy to prevent the recurrence of the disease state, wherein the oligonucleotide is administered in maintenance doses, ranging from 0.01 μg to 100 g per kg of body weight, once or more daily, to once every 20 years.

II. Drug Screening

In some embodiments, the present invention provides drug screening assays (e.g., to screen for anticancer drugs). In some embodiments, the screening methods of the present invention utilize the p53 mitochondrial targeting vectors described herein. For example, in some embodiments, the present invention provides methods of screening for compounds that refold functionally inactive mutant mitochondrial p53 proteins. In other embodiments, the present invention provides drug screening methods that screen for compounds that facilitate targeting of normal p53 to the mitochondria or enhance normal p53 expression in mitochondria. In some embodiments, candidate compounds are small molecules.

A. p53 Expression Assays

In one screening method, candidate compounds are evaluated for their ability to alter (e.g., increase) wild type p53 expression at mitochondria by contacting a compound with a cell and then assaying for the effect of the candidate compounds on mitochondrial p53 expression. In some embodiments, the effect of candidate compounds on mitochondrial expression of p53 is assayed for by detecting the level of mitochondrial p53 mRNA expressed by the cell. mRNA expression can be detected by any suitable method, including but not limited to, those disclosed herein.

In some embodiments, RNA is detected by Northern blot analysis. Northern blot analysis involves the separation of RNA and hybridization of a complementary labeled probe. Methods for Northern blot analysis are well known in the art.

In other embodiments, RNA expression is detected by enzymatic cleavage of specific structures (INVADER assay, Third Wave Technologies; See e.g., U.S. Pat. Nos. 5,846,717; 6,090,543; 6,001,567; 5,985,557; and 5,994,069; each of which is herein incorporated by reference). The INVADER assay detects specific nucleic acid (e.g., RNA) sequences by using structure-specific enzymes to cleave a complex formed by the hybridization of overlapping oligonucleotide probes.

In still further embodiments, RNA (or corresponding cDNA) is detected by hybridization to a oligonucleotide probe. A variety of hybridization assays using a variety of technologies for hybridization and detection are available. For example, in some embodiments, TaqMan assay (Applied Biosystems, Foster City, Calif.; See e.g., U.S. Pat. Nos. 5,962,233 and 5,538,848, each of which is herein incorporated by reference) is utilized. The assay is performed during a PCR reaction. The TaqMan assay exploits the 5'-3' exonuclease activity of the AMPLITAQ GOLD DNA polymerase. A probe consisting of an oligonucleotide with a 5'-reporter dye (e.g., a fluorescent dye) and a 3'-quencher dye is included in the PCR reaction. During PCR, if the probe is bound to its target, the 5'-3' nucleolytic activity of the AMPLITAQ GOLD polymerase cleaves the probe between the reporter and the quencher dye. The separation of the reporter dye from the quencher dye results in an increase of fluorescence. The signal accumulates with each cycle of PCR and can be monitored with a fluorimeter.

In yet other embodiments, reverse-transcriptase PCR (RT-PCR) is used to detect the expression of RNA. In RT-PCR, RNA is enzymatically converted to complementary DNA or "cDNA" using a reverse transcriptase enzyme. The cDNA is then used as a template for a PCR reaction. PCR products can be detected by any suitable method, including but not limited to, gel electrophoresis and staining with a DNA specific stain or hybridization to a labeled probe. In some embodiments, the quantitative reverse transcriptase PCR with standardized mixtures of competitive templates method described in U.S. Pat. Nos. 5,639,606, 5,643,765, and 5,876,978 (each of which is herein incorporated by reference) is utilized.

In other embodiments, the effect of candidate compounds is assayed by measuring the level of mitochondrial p53 polypeptide expression. The level of polypeptide expressed can be measured using any suitable method, including but not limited to, those disclosed herein. In some embodiments, proteins are detected by binding of an antibody specific for the protein. The present invention is not limited to a particular antibody. Any antibody (monoclonal or polyclonal) that specifically detects mitochondrial p53 may by utilized. Methods for the generation of antibodies are described below.

Antibody binding is detected by techniques known in the art. For example, in some embodiments antibody binding is detected using a suitable technique, including but not limited to, radioimmunoassay, ELISA (enzyme-linked immunosorbant assay), "sandwich" immunoassays, immunoradiometric assays, gel diffusion precipitation reactions, immunodiffusion assays, in situ immunoassays (e.g., using colloidal gold, enzyme or radioisotope labels, for example), Western blots, precipitation reactions, agglutination assays (e.g., gel agglutination assays, hemagglutination assays, etc.), complement fixation assays, immunofluorescence assays, protein A assays, and immunoelectrophoresis assays. In other embodiments, immunohistochemistry is utilized for the detection of antibody binding.

In one embodiment, antibody binding is detected by detecting a label on the primary antibody. In another embodiment, the primary antibody is detected by detecting binding of a secondary antibody or reagent to the primary antibody. In a further embodiment, the secondary antibody is labeled. Many methods are known in the art for detecting binding in an immunoassay and are within the scope of the present invention.

In some embodiments, an automated detection assay is utilized. Methods for the automation of immunoassays include, but are not limited to, those described in U.S. Pat. Nos. 5,885,530, 4,981,785, 6,159,750, and 5,358,691, each of which is herein incorporated by reference. In some embodiments, the analysis and presentation of results is also automated. For example, in some embodiments, software that generates a diagnosis and/or prognosis based on the presence or absence of a series of proteins corresponding to cancer markers is utilized.

In other embodiments, the immunoassay described in U.S. Pat. Nos. 5,599,677 and 5,672,480, each of which is herein incorporated by reference, is utilized. In other embodiments, proteins are detected by immunohistochemistry.

As described above, in some embodiments, the present invention provides methods of screening for compounds that refold functionally inactive mutant mitochondrial p53 proteins. As was shown by experiments described below, mutant p53 carrying tumor cells, proportional to their abnormally elevated total cellular levels of (mutant) p53 protein, have constitutively present mutant p53 at the mitochondria but it is functionally inactive (Mihara et al., Mol. Cell, 2003). Accordingly, in some embodiments, the cytochrome c release assay described in the Mihara paper provides a rapid drug screen to identify small molecule compounds that refold the mutant p53 in such a way that they regain mitochondrial biological function.

B. Cellular Assays

In contrast to normal cells or cancer cells with wild type p53, human cancer cells harboring mutant p53 genes express constitutively high levels of mutant p53 protein at the mitochondria. However, all 8 of 8 different tumor-derived p53 mutants tested failed to be functionally active at the mitochondria. In some preferred embodiments, the present invention provides methods of identifying small molecule activators of mutant mitochondrial p53. In some embodiments, cell lines with mutant p53 (e.g., cancer cell lines) are utilized and mitochondrial function of p53 and apoptosis are monitored.

The present invention is also not limited to a particular test compound. In some embodiments, lead compounds known to rescue mutant p53 for transcriptional function (e.g., including, but not limited to, CP-31398 and PRIMA-1) are utilized. However, the present invention is not limited to the use of CP-31398 and PRIMA-1. A variety of commercial sources and methods of generating test compounds are known in the art. The test compounds of the present invention can be obtained using any of the numerous approaches in combinatorial library methods known in the art, including biological libraries; peptoid libraries (libraries of molecules having the functionalities of peptides, but with a novel, non-peptide backbone, which are resistant to enzymatic degradation but which nevertheless remain bioactive; see, e.g., Zuckennann et al., J. Med. Chem. 37: 2678-85 [1994]); spatially addressable parallel solid phase or solution phase libraries; synthetic library methods requiring deconvolution; the 'one-bead one-compound' library method; and synthetic library methods using affinity chromatography selection. The biological library and peptoid library approaches are preferred for use with peptide libraries, while the other four approaches are applicable to peptide, non-peptide oligomer or small molecule libraries of compounds (Lam (1997) Anticancer Drug Des. 12:145).

Examples of methods for the synthesis of molecular libraries can be found in the art, for example in: DeWitt et al., Proc. Natl. Acad. Sci. U.S.A. 90:6909 [1993]; Erb et al., Proc. Nad. Acad. Sci. USA 91:11422 [1994]; Zuckermann et al., J. Med. Chem. 37:2678 [1994]; Cho et al., Science 261:1303 [1993]; Carrell et al., Angew. Chem. Int. Ed. Engl. 33.2059 [1994]; Carell et al., Angew. Chem. Int. Ed. Engl. 33:2061 [1994]; and Gallop et al., J. Med. Chem. 37:1233 [1994].

Libraries of compounds may be presented in solution (e.g., Houghten, Biotechniques 13:412-421 [1992]), or on beads (Lam, Nature 354:82-84 [1991]), chips (Fodor, Nature 364:555-556 [1993]), bacteria or spores (U.S. Pat. No. 5,223,409; herein incorporated by reference), plasmids (Cull et al., Proc. Nad. Acad. Sci. USA 89:18651869 [1992]) or on phages (Scott and Smith, Science 249:386-390 [1990]; Devlin Science 249:404-406 [1990]; Cwirla et al., Proc. Natl. Acad. Sci. 87:6378-6382 [1990]; Felici, J. Mol. Biol. 222:301 [1991]).

C. In Vivo Assays

In still further embodiments, animal models (e.g., cancer models) are utilized in drug screening applications. Exemplary animals are described in the Experimental section (e.g., lymphoma model). In some embodiments, p53 targeting vectors are tested in animal models of cancer. In other embodiments, small molecules (e.g., those described above) are tested in animal models.

III. Antibodies

The present invention provides isolated antibodies against p53. These antibodies find use, for example, in the drug screening methods described herein.

An antibody against a protein of the present invention may be any monoclonal or polyclonal antibody, as long as it can recognize the protein. Antibodies can be produced by using a protein of the present invention as the antigen according to a conventional antibody or antiserum preparation process.

The present invention contemplates the use of both monoclonal and polyclonal antibodies. Any suitable method may be used to generate the antibodies used in the methods and compositions of the present invention, including but not limited to, those disclosed herein. For example, for preparation of a monoclonal antibody, protein, as such, or together with a suitable carrier or diluent is administered to an animal (e.g., a mammal) under conditions that permit the production of antibodies. For enhancing the antibody production capability, complete or incomplete Freund's adjuvant may be administered. Normally, the protein is administered once every 2 weeks to 6 weeks, in total, about 2 times to about 10 times. Animals suitable for use in such methods include, but are not limited to, primates, rabbits, dogs, guinea pigs, mice, rats, sheep, goats, etc.

For preparing monoclonal antibody-producing cells, an individual animal whose antibody titer has been confirmed (e.g., a mouse) is selected, and 2 days to 5 days after the final immunization, its spleen or lymph node is harvested and antibody-producing cells contained therein are fused with myeloma cells to prepare the desired monoclonal antibody producer hybridoma. Measurement of the antibody titer in antiserum can be carried out, for example, by reacting the labeled protein, as described hereinafter and antiserum and then measuring the activity of the labeling agent bound to the antibody. The cell fusion can be carried out according to known methods, for example, the method described by Koehler and Milstein (Nature 256:495 [1975]). As a fusion promoter, for example, polyethylene glycol (PEG) or Sendai virus (HVJ), preferably PEG is used.

Examples of myeloma cells include NS-1, P3U1, SP2/0, AP-1 and the like. The proportion of the number of antibody producer cells (spleen cells) and the number of myeloma cells to be used is preferably about 1:1 to about 20:1. PEG (preferably PEG 1000-PEG 6000) is preferably added in concentration of about 10% to about 80%. Cell fusion can be carried out efficiently by incubating a mixture of both cells at about 20° C. to about 40° C., preferably about 30° C. to about 37° C. for about 1 minute to 10 minutes.

Various methods may be used for screening for a hybridoma producing the antibody (e.g., against p53). For example, where a supernatant of the hybridoma is added to a solid phase (e.g., microplate) to which antibody is adsorbed directly or together with a carrier and then an anti-immunoglobulin antibody (if mouse cells are used in cell fusion, anti-mouse immunoglobulin antibody is used) or Protein A labeled with a radioactive substance or an enzyme is added to detect the monoclonal antibody against the protein bound to the solid phase. Alternately, a supernatant of the hybridoma is added to a solid phase to which an anti-immunoglobulin antibody or Protein A is adsorbed and then the protein labeled with a radioactive substance or an enzyme is added to detect the monoclonal antibody against the protein bound to the solid phase.

Selection of the monoclonal antibody can be carried out according to any known method or its modification. Normally, a medium for animal cells to which HAT (hypoxanthine, aminopterin, thymidine) are added is employed. Any selection and growth medium can be employed as long as the hybridoma can grow. For example, RPMI 1640 medium containing 1% to 20%, preferably 10% to 20% fetal bovine serum, GIT medium containing 1% to 10% fetal bovine serum, a serum free medium for cultivation of a hybridoma (SFM-101, Nissui Seiyaku) and the like can be used. Normally, the cultivation is carried out at 20° C. to 40° C., preferably 37° C. for about 5 days to 3 weeks, preferably 1 week to 2 weeks under about 5% $CO_2$ gas. The antibody titer of the supernatant of a hybridoma culture can be measured according to the same manner as described above with respect to the antibody titer of the anti-protein in the antiserum.

Separation and purification of a monoclonal antibody (e.g., against p53) can be carried out according to the same manner as those of conventional polyclonal antibodies such as separation and purification of immunoglobulins, for example, salting-out, alcoholic precipitation, isoelectric point precipitation, electrophoresis, adsorption and desorption with ion exchangers (e.g., DEAE), ultracentrifugation, gel filtration, or a specific purification method wherein only an antibody is collected with an active adsorbent such as an antigen-binding solid phase, Protein A or Protein G and dissociating the binding to obtain the antibody.

Polyclonal antibodies may be prepared by any known method or modifications of these methods including obtaining antibodies from patients. For example, a complex of an immunogen (an antigen against the protein) and a carrier protein is prepared and an animal is immunized by the complex according to the same manner as that described with respect to the above monoclonal antibody preparation. A material containing the antibody against is recovered from the immunized animal and the antibody is separated and purified.

As to the complex of the immunogen and the carrier protein to be used for immunization of an animal, any carrier protein and any mixing proportion of the carrier and a hapten can be employed as long as an antibody against the hapten, which is crosslinked on the carrier and used for immunization, is produced efficiently. For example, bovine serum albumin, bovine cycloglobulin, keyhole limpet hemocyanin, etc. may be coupled to an hapten in a weight ratio of about 0.1 part to about 20 parts, preferably, about 1 part to about 5 parts per 1 part of the hapten.

In addition, various condensing agents can be used for coupling of a hapten and a carrier. For example, glutaraldehyde, carbodiimide, maleimide activated ester, activated ester reagents containing thiol group or dithiopyridyl group, and the like find use with the present invention. The condensation product as such or together with a suitable carrier or diluent is administered to a site of an animal that permits the antibody production. For enhancing the antibody production capability, complete or incomplete Freund's adjuvant may be administered. Normally, the protein is administered once every 2 weeks to 6 weeks, in total, about 3 times to about 10 times.

The polyclonal antibody is recovered from blood, ascites and the like, of an animal immunized by the above method. The antibody titer in the antiserum can be measured according to the same manner as that described above with respect to the supernatant of the hybridoma culture. Separation and purification of the antibody can be carried out according to the same separation and purification method of immunoglobulin as that described with respect to the above monoclonal antibody.

The protein used herein as the immunogen is not limited to any particular type of immunogen. For example, p53 protein (further including a gene having a nucleotide sequence partly altered) can be used as the immunogen. Further, fragments of the protein may be used. Fragments may be obtained by any methods including, but not limited to expressing a fragment of the gene, enzymatic processing of the protein, chemical synthesis, and the like.

In some embodiments, antibodies (e.g., monoclonal antibodies) are humanized. Such humanized antibodies find particular use in the cancer immunotherapies described below. Humanized antibodies are altered in order to make them less immunogenic to humans, e.g., by constructing chimeric antibodies in which a mouse antigen-binding variable domain is coupled to a human constant domain. Humanized antibodies are typically human antibodies in which some CDR residues and possibly some FR residues are substituted by residues from analogous sites in rodent antibodies. Methods for humanizing antibodies are well known in the art and include but are not limited to, those disclosed in U.S. Pat. Nos. 6,054,297, 4,816,567, 6,180,377, 5,871,907, 5,585,089, and 6,180,370, each of which is herein incorporated by reference.

EXPERIMENTAL

The following examples are provided in order to demonstrate and further illustrate certain preferred embodiments and aspects of the present invention and are not to be construed as limiting the scope thereof.

In the experimental disclosure which follows, the following abbreviations apply: N (normal); M (molar); mM (millimolar); μM (micromolar); mol (moles); mmol (millimoles); μmol (micromoles); nmol (nanomoles); pmol (picomoles); g (grams); mg (milligrams); μg (micrograms); ng (nanograms); l or L (liters); ml (milliliters); μl (microliters); cm (centimeters); mm (millimeters); μm (micrometers); nm (nanometers); and ° C. (degrees Centigrade).

EXAMPLE 1

Mitochondrial Targeted p53

This example describes the mitochondrial targeting of p53 in vitro and in vivo.

A. Materials and Methods

Retroviral constructs. The replication-defective mouse stem cell virus MSCV/CMV-GFP Bla was constructed by cloning green fluorescent protein fused with Blasticidine S-deaminase downstream of the MSCV polylinker. GFP Bla is driven by a separate CMV promoter, since attempts to drive it from the p53-driving LTR promoter via an internal ribosomal entry site were unsuccessful despite p53 expression. The following cDNAs were subcloned into this vector at EcoRI/Not I sites: human wild type p53 (Nucl p53), wild type p53 fused at its C-terminus to the transmembrane domain of BclXL (p53CTB) or Bcl2 (p53CTM), respectively, or to the ER leader sequence of cytochrome b5 (p53ER) and the isolated transmembrane domain of BclXL without p53. Retroviral stocks were produced in PhoenixE cells (Petrenko et al., Mol Cell Biol 23:5540-5555).

Lymphoma model. Eμ myc transgenic mice (C57BL/6-TgMyc) were crossed with p53+/− mice or INK4a/ARF+/− mice and offspring were genotyped by PCR (Jacks et al., 1994. Curr. Biol. 4:1-7). In 90% of p53+1− and ARF+I− animals, lymphomas were present at 30-50 days (Schmitt et al., 1999. Genes Dev 13:2670-2677) and 80% of tumors had lost their remaining wild type p53 or INK4a/ARF allele. These lymphomas are transplantable into normal syngeneic mice where they fully reproduce their biological behavior (Schmitt et al., supra). Lymphomas were harvested from tumor-bearing lymph nodes of donors. Cells were immunophenotyped by FACS as Thy12−, B220+ and IgM− (pre B-cell) or IgM+ (mature B-cell lymphoma). Primary tumor cells were cultured for 3 days to eliminate normal cell contamination. Re-genotyping confirmed the loss of the remaining alleles in all isolates, giving rise to p53−/− ARF+/+ or p53+/+ ARF−/− lymphomas. Independent isolates derived from 6 mice were used. Cell suspensions were plated on mitomycin-arrested NIH3T3 feeders and grown in 45% Iscove's medium, 45% Dulbecco's medium, 10% FBS prior to spinocculation (Schmitt et al., 2000. Nat. Med. 6:1029-1035).

Mouse embryonic fibroblasts (MEFs) were prepared from 14.5 d embryos (C57BL/6). p53−/− MEFs were derived from Trp53tm1Tyj mutant mice. MEFs and NIH 3T3 were maintained in DME medium plus 10% FBS. In vitro growth of infected lymphoma cells was measured by plating equal numbers in triplicate on equal numbers of feeders, with daily counting of non-adherent cells by Coulter counter and FACS. For focus formation assays, MEFs were infected with E1A expressing retrovirus (Petrenko et al., supra), followed by empty virus, p53CTM or p53CTB virus 36 hours later. Cells were selected in blasticidin for 2 days and transduced with H-RasV12 (Petrenko et al., supra). After 16 days, Giemsa-stained foci were counted. For in vitro apoptosis studies, samples were initially adjusted to 65% of GFP-positive cells. For lymphoma cells, TUNEL (Roche, Nutley, N.J.) was performed 36 h after transduction without additional DNA damage. For MEFs, E1A-sensitized cells were transduced, then selected by blasticidine for 2 days to obtain 100% GFP-positivity, and either left untreated or treated with Adriamycin (0.34 μM) for 6 or 12 hrs.

Protein expression. Whole cell lysates (50-70 μg) were immunoblotted with antibodies specific for p53 (mouse-specific CM-5, Vector, Burlingame, Calif.) (human-specific DO-1 Calbiochem, Darmstadt, Germany); p21 (SXM30, Pharmingen, San Diego, Calif.), PUMAα, β (AbCam Cambridge, Mass.); p19ARF (Ab80-50, AbCam); p21 (F5), MDM2 (SMP14), BclXL/xs (S18), E1A (135-5) and PCNA (all Santa Cruz Biotechn., Santa Cruz, Calif.).

Immunofluorescence. Lymphoma cells were cytospun onto slides; 3T3 cells were grown in 8-well chamber slides. Cells were fixed in 4% paraformaldehyde for 20 min and permeabilized with PBS/0.5% Tween 20 for 5 min. Slides were blocked in 10% normal goat serum, followed by 2 h incubation with CM-1 (1:500; human specific p53, Vector) and either cytochrome c, (1:200; clone 2G8) or mt hsp70 (1:25; ABR Affinity Bioreagents Golden, Colo.) to detect mitochondria. For p53ER, p53 was detected with DO-1 and ER was detected with anti-calreticulin (ABR). Anti-mouse IgG and anti-rabbit IgG were used for controls. Slides were incubated in Cy5- and TRITC-conjugated secondary antibodies for 1 hr. Cells were viewed in a confocal laser microscope (ZEISS LSM 510). Tumor sections were stained with DO-1 by immunoperoxidase.

In vivo competition experiments. Three different protocols using GFP-positive ratios of 40:60, 75:25 and 90:10 were employed as described in results. FACS sorted cells were cultured for 3 days prior to injection to verify sterility. $1 \times 10^6$ lymphoma cells in 100 μl PBS were injected into the tail vein of syngeneic, nontransgenic recipient mice. After 26-30 days, animals had developed palpable lymphomas in the cervical and/or inguinal, axillary and retroperitoneal regions. Occasionally, extranodal lymphomas were seen. From each recipient, all tumors were pooled and FACS analyzed to determine residual GFP-positivity. To verify histopathology, each tumor was processed for H&E. In no case were inflammatory lymphocytic infiltrates within or around the tumors observed. Likewise, damage of normal tissue components including vasculature and stroma was not present. For apoptosis assays in vivo, lymphomas were fixed and stained by TUNEL with Hoechst counterstaining. Alternatively, $2 \times 10^6$ transduced lymphoma cells were injected subcutaneously into normal syngeneic mice and animals sacrificed 2, 4, 8 and 12 days later. Injection sites were harvested and processed for TUNEL/H&E and p53 immunoperoxidase staining with DO-1.

B. Results

Characterization of primary lymphoma isolates and retroviruses for in vivo studies. Eμ myc transgenic mice overexpress the c-myc oncogene in their B-cell lineage and develop pre-B and B-cell lymphomas within 4-6 months of age (Harris et al., 1988 J. Exp. Med. 167:353-371). This well established transplantable tumor model has many advantages (FIG. 1). In addition, test genes can be efficiently introduced ex vivo by retroviral gene transfer into isolated primary lymphoma cells and injected into the tail vein of normal syngeneic recipient mice for lymphoma reconstitution. Tumor formation and aggressiveness depends on a disabled p53 pathway (Schmitt et al., 1999, Genes Dev 13:2670-2677; Schmitt et al., 2000 Nat Med 6:1029-1035; Eischen et al., 2001, Mol Cell Biol 21:7653-7662; Eischen et al., 2001, Mol Cell Biol 21:5063-5070; Eischen et al., 1999, Genes Dev 13:2658-2669; Jacobs et al., 1999, Genes Dev. 13:2678-2690.). Tumor apoptosis occurs via the mitochondrial pathway, since Bcl2, which is not overexpressed in these lymphomas, produces multi-drug resistance when forcibly overexpressed (Schmitt et al., 2000, supra). Loss of p53 is equivalent to loss of INK4a/ARF, the positive upstream regulator of p53, and both events greatly accelerate c-myc lymphomagenesis (Schmitt et al., 1999, supra). Compared to parental tumors, p53- and ARF-null lymphomas are highly invasive with severe apoptotic defects and marked resistance to chemotherapy (Schmitt et al., 1999, supra).

Figure 6:
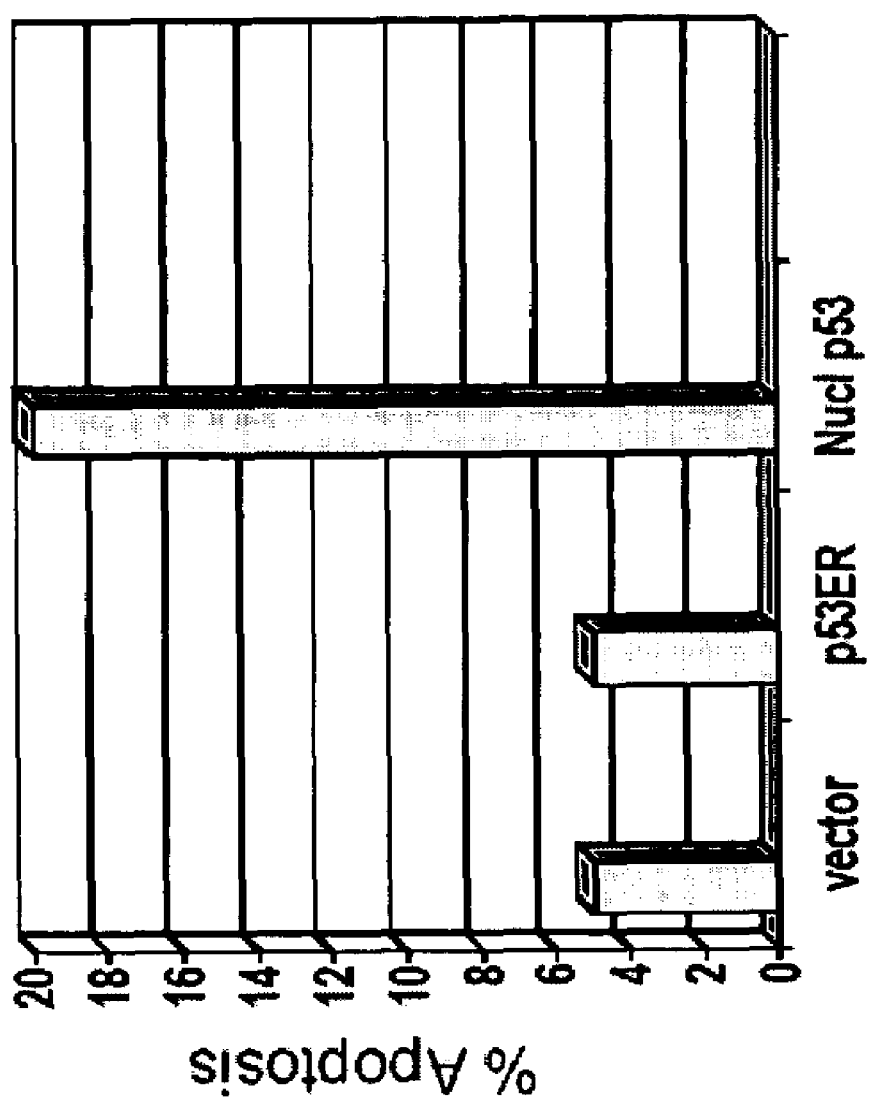
FIG. 6 shows targeting of p53 to the endoplasmic reticulum by fusing its C-terminus with the ER leader sequence of human cytochrome b5.

Four independent p53−/− ARF+/+ and two ARF−/− p53+/+ B-lymphomas were isolated from p53+/− and ARF+/− Eμ myc mice (FIG. 2a). Isolates were transduced with murine stem cell virus expressing GFP and either conventional p53 (Nuclearp53), or 2 versions of mitochondrially targeted p53 via fusion with the transmembrane domain of BclXL (p53CTB) or Bcl2 (p53CTM). Control virus lacked p53 inserts (FIG. 2a). Infection efficiency was around 40% for all constructs (FIG. 2d). In p53 null and ARF null lymphoma and in NIH3T3 cells expression levels of p53CTM and p53CTB are equivalent to the physiologic stress-induced p53 levels of normal irradiated thymocytes (FIG. 2b left). Levels of Nuclp53 were slightly lower than targeted p53CTM (FIG. 2b right and FIG. 2c).

p53CTB and p53CTM target to mitochondria. Localization studies demonstrated that p53CTB localized exclusively to mitochondria in all cell types tested, in agreement with exclusive mitochondrial localization of native BclXL (Kaufmann et al., 2003, J Cell Biol 160:53-64). p53CTM exhibited a predominant mitochondrial localization (Mihara et al., 2003, Mol Cell. 11:577-590), plus some minor localization to endoplasmic reticulum (ER), consistent with native Bcl2 localization (Kaufmann et al., 2003, supra). To rule out that the ER-localized fraction of p53CTM contributes to apoptosis, p53 was targeted to the ER by replacing the Bcl2 domain with the ER leader sequence of cytochrome b5. p53ER lacked any apoptotic ability in p53 null H1299 and SaOS-2 cells, indicating that the apoptotic ability of p53CTM was solely due to its mitochondrial action (FIG. 6).

To further rule out that the short mitochondrial targeting peptide alone (derived from BclXL) could induce lymphoma cell death when ectopically expressed, a retrovirus was constructed containing only the transmembrane domain of human BclXL: L S R K G Q E R F N R W F L T G M T V A G V V L L G S L F S R K * (SEQ ID NO:9) as an insert. However, p53 null lymphoma cells infected with this virus failed to undergo any apoptosis.

Mitochondrially targeted p53 promotes apoptosis in primary lymphoma cells in vitro. The apoptotic ability of p53CTB and p53CTM in vitro on primary mouse embryo fibroblasts and lymphoma isolates was first analyzed. Wild type, p53 null and ARF null MEFs were pre-sensitized to cell death by E1A. After treatment with adriamycin for 6 and 12 hrs, mitochondrial p53CTB and p53CTM proteins increased apoptosis by about 2-fold in all three genotypes, compared to vector alone (FIG. 3a). Mitochondrial p53 suppressed transformation of MEFs by E1A and oncogenic H-RasV12. The number of foci was reduced by almost 50% in the presence of p53CTB or p53CTM compared to empty virus. More importantly, p53CTM and p53CTB restrain growth of primary p53 null lymphoma cells, leading to a 4-fold reduction in cell numbers over vector after 5 days (FIG. 4a). Likewise, in growth competition assays the numbers of p53CTM- and Nuclp53-infected lymphoma cells sharply declined over 10 to 25 days, while empty virus-infected cells dropped only slightly (FIG. 4b). The loss of p53CTM-and p53CTB-expressing lymphoma cells in vitro is due to p53-induced apoptosis, as indcted by TUNEL assays, since their expression, without additional DNA damage, doubles spontaneous apoptosis over empty virus.

Figure 3B:
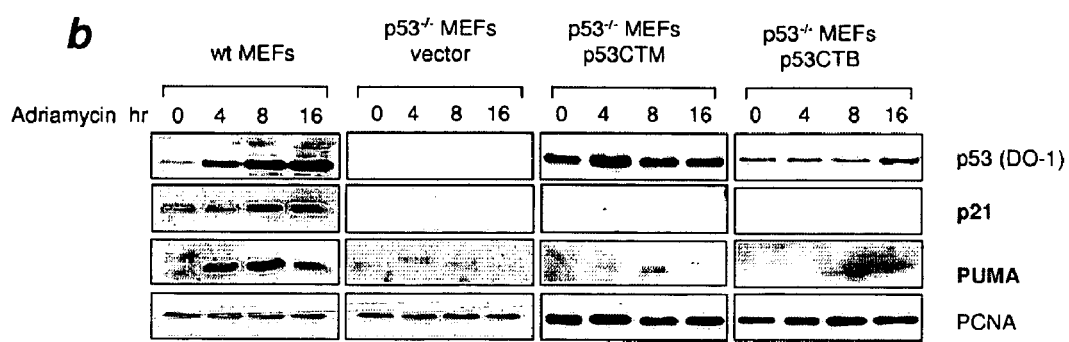
Figure 4C:
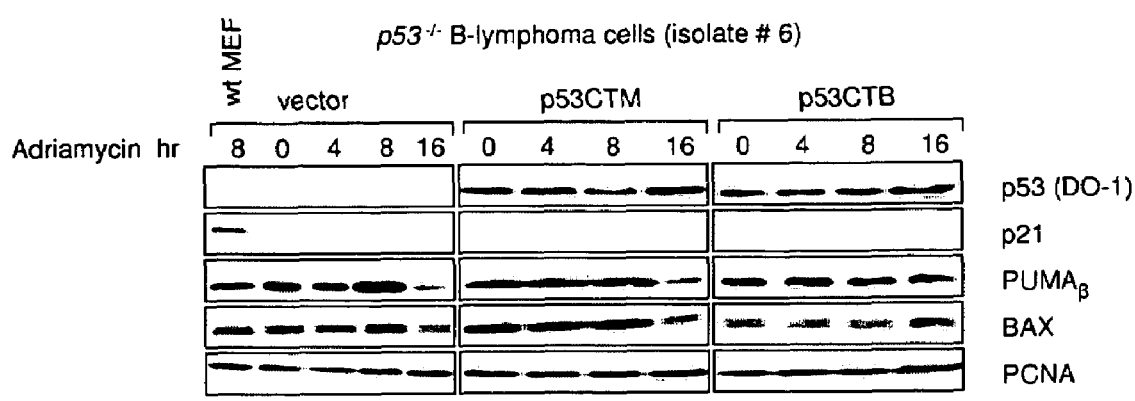
FIG. 4c shows that mitochondrially targeted p53 proteins lack transcriptional activity.
Figure 7:
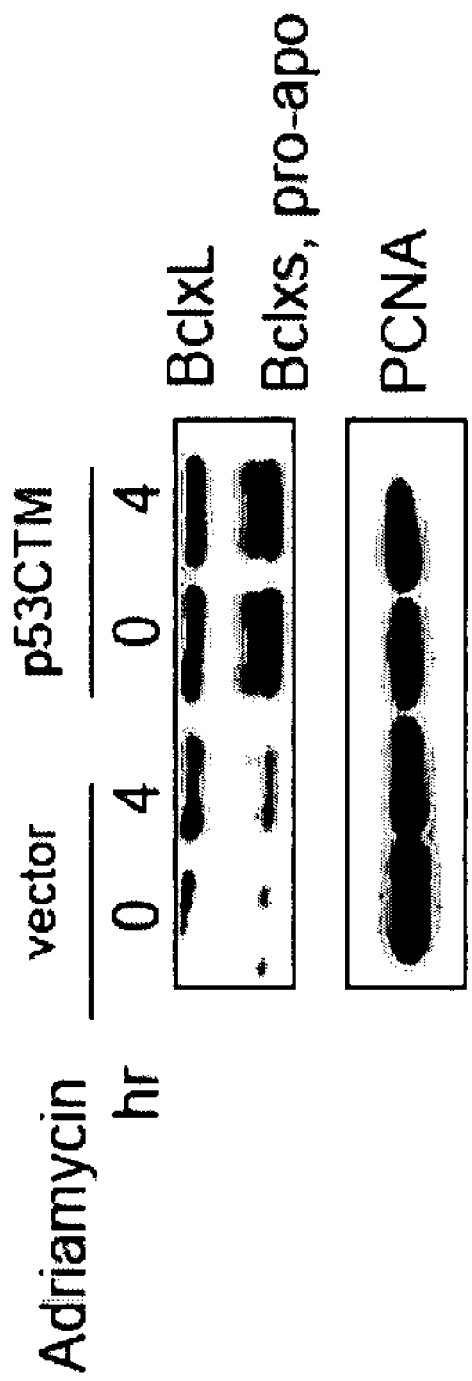
FIG. 7 shows that compared to vector-transduced p53 null lymphoma cells, cells expressing mitochondrially targeted p53 express greatly increased levels of the BclXs isoforms, which are alternate splice products of the BclX gene that lack the internal BH1 and BH2 domains and promote apoptosis.

Mitochondrially targeted p53 lacks transcriptional activity. p53CTB and p53CTM proteins were undetectable in nuclei of all cells tested including p53−/− and ARF−/− lymphoma cells, MEFs of all 3 genotypes, NIH3T3 and H1299 cells. To rule out residual transcriptional activity of these proteins, their ability to induce endogenous target genes of the apoptotic and arrest category was analyzed. p53CTM and p53CTB were unable to induce PUMA, Bid or p21Waf1 in p53 null MEFs, even in the presence of the DNA damaging agent adriamycin (FIG. 3b). p53CTM and p53CTB also lack residual transcriptional activity in p53 null lymphoma cells, as indicated by PUMA, Bax, p21Waf1 and MDM2 (FIG. 4c). Compared to empty virus, p53CTM transduced lymphomas increased their level of BclXs isoforms, pro-apoptotic alternate splice products of the Bcl-X gene that lack the internal BH1/BH2 domains (Lindenboim et al., 2001, Cell Death Differ 8:933-942; Boise et al., L.H., 1993, Cell 74:597-608) (FIG. 7). Together, these data confirm that the apoptotic potency of p53CTB/CTM is due to their direct action at the mitochondria, and not due to a cryptic transcription-dependent p53 function.

Mitochondrially Targeted p53 Kills Primary Lymphoma Cells In Vivo.

To assess the impact of mitochondrially targeted p53 on tumor cell apoptosis and tumor burden in vivo, transduced lymphoma cells were injected into the tail veins of syngeneic normal recipients, where they produced again nodal and sometimes extranodal lymphomas within 26-30 days. Thus, the rapidly reconstituted lymphomas differed only by the presence or absence of p53 proteins (Schmitt et al., 2000, supra). In the context of p53 null lymphomas, this model provides a quantitative measure of whether mitochondrial p53, as the sole source of cellular p53, has efficient tumor killing actions in vivo to cause tumor regression at natural sites. Mouse and human p53 are functionally interchangeable in vivo, since knock-in mice harboring the human p53 DNA binding domain within a mouse gene backbone have unaltered p53 function (Luo et al., 2001, Oncogene 20:320-328).

All experiments were performed as in vivo competitions between transduced and parental cells, using 3 different protocols. In the first protocol, 40% of freshly transduced p53 null lymphoma cells, confirmed for GFP-positivity at 36 hours (FIG. 2d), were mixed with 60% GFP-negative parental lymphoma cells and immediately injected into recipients (1×10$^6$ per mouse). Four weeks later, reconstituted tumors were pooled for each recipient and their residual GFP positivity determined by FACS (Table I (shown in FIG. 11)). Eighteen mice injected with 40% empty virus-GFP yielded 30.8%+/–18% residual GFP-positive tumors, reflecting the ability of vector-transduced cells to survive in the bloodstream and proportionally contribute to lymphoma reconstitution. The 14 mice receiving 40% p53CTM-GFP transduced cells yielded tumors with only 2.8+/–2.4% residual GFP-positive cells. The individual tumor GFP+ scores of the p53CTM group were 0%, 0%, 0%, 0%, 0%, 0%, 0%, 0%, 0%, 0%, 0.6%, 1.5%, 3.5% and 34%, respectively (P<0.0005 compared to empty virus group) (FIG. 5). When the single atypical animal with 34% GFP-positivity was deleted because analysis suggested that it expressed a functionally inactive p53 (see FIG. 8), the p53CTM group dropped to 0.4+/–1.0% GFP-positivity (P<0.0001 compared to vector group). Likewise, 4 mice injected with 40% p53CTB-GFP expressing cells yielded tumors without detectable residual green cells (individual GFP scores were 0%, 0%, 0% and 0%) (FIG. 5). Thus, 82% of reconstituted tumors were completely (14/17 mice) and 18% almost completely (3/17 of mice) devoid of tumor cells expressing mitochondrially targeted p53. Instead, tumors were composed of surviving parental cells. Each of 12 control mice injected with 40% Nuclp53-expressing cells also yielded 0% residual GFP positivity due to efficient p53-mediated apoptosis during tumor reconstitution. Together, this indicates that lymphoma cells expressing mitochondrial p53 as their sole source of p53 can undergo dramatic tumor regression in vivo, which is nearly as efficient as the regression achieved with ectopic nuclear p53.

Subsequent competition protocols using higher proportions of transduced versus parental lymphoma cells confirmed the in vivo killing ability of mitochondrially targeted p53. Transduced cells were either drug selected or FACS sorted prior to injection to obtain a higher percentage than could be achieved by transduction alone. In the 75:25 protocol, transduced p53 null cells were first pre-selected in blasticidine for 4-10 days (Table I (shown in FIG. 11)). This quickly eliminates cells with high p53 expression and enriches for cells with low expression that are able to survive longer in culture. Once in vivo, these cells probably receive additional physiological stress signals that trigger their apoptosis. Mixtures of 75% transduced and 25% parental cells were injected into normal recipients. Three mice injected with 75% vector-GFP cells yielded tumors with 44.3%+/–3% GFP-positivity, reflecting a decreased but still strong ability of these cells to contribute to lymphomas. In contrast, 11 mice injected with 75% p53CTM-GFP cell mixtures yielded tumors containing only 1.1+/–0.1% residual GFP-positivity (P<0.0005 compared to empty virus), confirming the p53CTM result seen in the 40:60 protocol. The positive control animal injected with 75% Nuclp53-GFP cells generated 12% residual GFP-positivity. Further analysis, however, showed that this tumor had selectively lost p53 expression due to rearrangement of the retroviral p53 region, which explained the relatively high numbers of surviving GFP-positive cells (FIG. 8).

Figure 8:
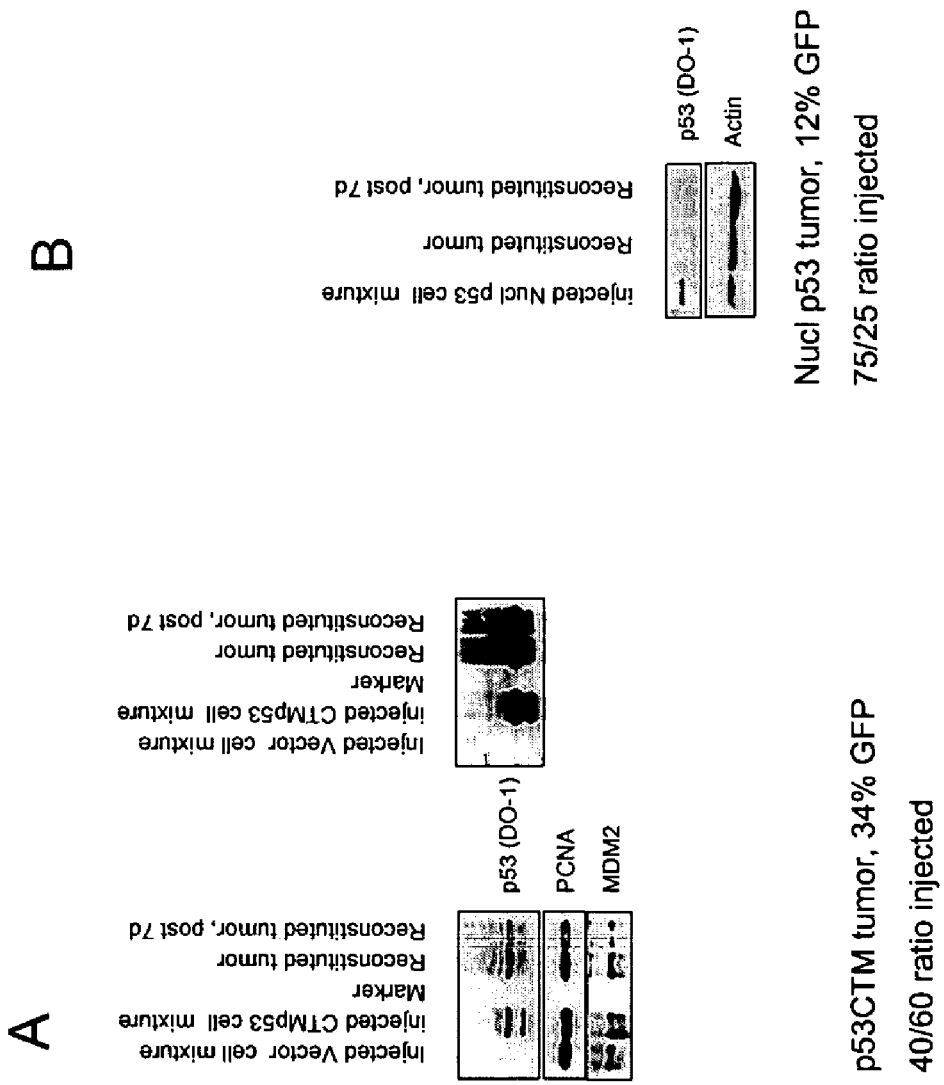
FIG. 8 shows characterization of rare outlier tumors in which p53CTM or Nuclp53-expressing viruses failed to kill tumor cells.

FIG. 8 shows characterization of rare outlier tumors in which p53CTM or Nuclp53-expressing viruses failed to kill tumor cells. Mice (n=13) injected with p53 null lymphoma cells containing 40% p53CTM-infected cells yielded tumors with an average of only 0.4+/–1.0% residual GFP-positive cells (Table I, FIG. 11). (a) However, a single additional tumor was exceptional because it showed only a minimal decrease to 34% GFP-positivity. Full length sequencing of p53CTM from reconstituted tumors ruled out that a mutation had been selected in vivo. Immunoblot analysis of originally injected and reconstituted tumor cells reveals that the p53 protein in this tumor had undergone abnormal posttranslational modification reminiscent of ubiquitylation. A tight ladder of higher molecular weight p53 bands are present in freshly harvested reconstituted tumor lysate (lanes 4, 9) whose expression is stable in culture (lanes 5, 10). This p53 is also spontaneously stabilized. The recovered tumor cells rapidly increased their 34% GFP score to 99% within 3 days in culture. The initially injected cells expressed almost exclusively non-modified p53 (lanes 2, 7). Despite p53 stabilization (lanes 4, 5), MDM2 and Arf protein levels remained unchanged. The present invention is not limited to a particular mechanism. Indeed, an understanding of the mechanism is not necessary to practice the present invention. Nonetheless, it is contemplated that taken together with its disabled apoptotic function, the p53 protein in this tumor appears to be functionally inactive.

Mice (n=12) injected with p53 null lymphoma cells containing 40% nuclear p53-infected cells yielded tumors with 0% residual GFP-positivity, due to p53-mediated apoptosis of these cells. (b) One animal injected with 75% nuclear p53-infected cells produced tumors with 12% residual GFP-positivity. Immunoblot analysis shows a complete loss of nuclear p53 expression in this tumor, indicating that this tumor had undergone rearrangement of its retroviral p53 sequence.

In the third protocol, transduced cells at their peak expression at 48 h post-infection were FACS-sorted by GFP to >99% purity. Sorted cells were mixed with parental cells at a 90 to 10 ratio and immediately injected into recipients. 14 control mice injected with 90% vector-GFP infected cells produced tumors with 70+/−10% GFP-positivity, while 7 mice injected with 90% p53CTM-transduced cells produced tumors averaging only 14+/−14% residual GFP-positivity (Table I (shown in FIG. 11)).

The reduction in the p53CTM group was again highly significant (P<0.0005 compared to empty virus). The transduced cells injected into the p53CTM group all originated from a single isolate (#3). Reconstituted tumors, however, fell into 2 subgroups. Tumors from 4 animals showed the expected strong reduction of p53CTM-expressing cells, with residual GFP scores of 2%, 2%, 3.5% and 5%. Three mice, however, showed only a moderate reduction, with scores of 26%, 28% and 36% GFP positivity. The present invention is not limited to a particular mechanism. Indeed, an understanding of the mechanism is not necessary to practice the present invention. Nonetheless, it is contemplated that one possible explanation for this bimodal distribution is that parental isolate #3 was genetically heterogeneous and contained a clonal subpopulation that had acquired an additional apoptotic mutation during lymphomagenesis in the donor. This latter clone might have become stochastically dominant in the three animals with relatively high GFP scores, but not in the four animals with low scores. In aggregate, these data confirm that mitochondrially targeted p53, as the sole source of cellular p53, has tumor killing actions in vivo at natural tumor sites. Moreover, this killing action does not require additional radio- or chemotherapeutic agents.

Despite the presence of a wild type p53 gene, ARF null lymphomas exhibit a strongly disabled p53 activity towards oncogenic deregulation (Schmitt et al., 1999, supra; Eischen et al., supra). To test whether targeted p53 also kills these cells in vivo, two independent ARF null tumor isolates were used in the competitive 40/60 protocol (FIG. 2b and Table II (shown in FIG. 12). Generally, a higher sensitivity to spontaneous and p53-induced cell death was found in ARF null lymphoma cells compared to p53 null lymphoma cells. Mice (n=14) injected with 40% empty virus-infected cell mixtures produced reconstituted tumors with 18+/−13% GFP-positivity. In contrast, mice (n=12) injected with 40% p53CTM-expressing cell mixtures produced tumors with only 0.2+/−0.4% residual GFP positivity (P=0.0001). Likewise, mice (n=11) injected with 40% p53CTB-expressing cell mixtures produced tumors with only 0.4+/−0.7% residual GFP-positivity (P=0.0001). The p53CTB and p53CTM rates were identical to the positive control of mice (n=13) injected with nuclear p53 (0.6%+/−0.6% residual GFP positivity). Thus, as in p53 null lymphomas, ARF null lymphomas expressing mitochondrially targeted p53 show a dramatic in vivo regression. Moreover, in these cells the mitochondrial p53 program can functionally override the disabled endogenous p53 program. As a further control of the specificity of tumor cell killing mediated by mitochondrially targeted p53, Table 3 (shown in FIG. 15) shows that 1) a naturally occurring mutant p53, in contrast to nuclear or mitochondrial wt p53, does not kill lymphoma cells but enables their expansion in vivo. It also shows that 2) the killing of mouse tumor cells with human versions of nuclear or mitochondrial wt p53 is specific and not due to a non-specific immune rejection.

All publications and patents mentioned in the above specification are herein incorporated by reference. Various modifications and variations of the described method and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention that are obvious to those skilled in the relevant fields are intended to be within the scope of the following claims.

We claim:

1. A method for delivering p53 to mitochondria in vitro comprising
   a) providing (i) a cell in vitro, wherein said cell lacks functional mitochondrial p53; and (ii) a vector comprising a p53 gene fused to a mitochondrial targeting sequence, wherein the vector comprises the nucleic acid sequence of SEQ ID NO: 1; and
   b) delivering said vector to said cell, wherein said delivery results in apoptosis of said cell.

2. The method of claim 1, wherein said vector encodes a fusion protein having the amino acid sequence of SEQ ID NO:2.

3. The method of claim 1, wherein said cell is a cancer cell.

4. The method of claim 1, further comprising delivering a second exogenous p53 gene to the nucleus of said cell.

5. The method of claim 4, wherein said second exogenous p53 gene is contained in a second vector, and wherein said second vector comprises a second sequence that directs said second exogenous p53 gene to the nucleus of said cell.

6. The method of claim 1, further comprising the step of delivering a test compound to said cell.

7. A nucleic acid comprising an exogenous p53 gene operably linked to a gene encoding a mitochondrial targeting protein, wherein said nucleic acid comprises SEQ ID NO:1.

8. A vector comprising the nucleic acid of claim 7.

9. The vector of claim 8 comprising a nucleic acid encoding a fusion protein having the amino acid sequence of SEQ ID NO:2.

10. An isolated cell comprising the vector of claim 8.

11. The cell of claim 10, wherein said cell is a cancer cell.

* * * * *